US007736891B2

(12) United States Patent

Nelson et al.

(10) Patent No.: US 7,736,891 B2

(45) Date of Patent: Jun. 15, 2010

(54) MICROFLUIDIC ASSAY SYSTEM WITH DISPERSION MONITORING

(75) Inventors: Kjell E. Nelson, Seattle, WA (US); Paul Yager, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 12/209,155

(22) Filed: Sep. 11, 2008

(65) Prior Publication Data

US 2009/0068760 A1 Mar. 12, 2009

Related U.S. Application Data

(60) Provisional application No. 60/971,463, filed on Sep. 11, 2007.

(51) Int. Cl.

| | |
|---|---|
| ***C12M 1/34*** | (2006.01) |
| ***C12M 3/00*** | (2006.01) |
| ***C12Q 1/00*** | (2006.01) |
| ***G01N 15/06*** | (2006.01) |
| ***G01N 33/00*** | (2006.01) |
| ***G01N 33/48*** | (2006.01) |
| ***G01N 33/53*** | (2006.01) |

(52) U.S. Cl. ....................... 435/288.5; 422/68.1; 435/4; 435/7.1; 435/287.1; 435/287.9; 435/288.2

(58) Field of Classification Search ....................... None
See application file for complete search history.

(56) References Cited

U.S. PATENT DOCUMENTS 5,023,053 A * 6/1991 Finlan ..................... 422/82.05

(Continued)

FOREIGN PATENT DOCUMENTS

WO WO2006/047591 * 5/2006

OTHER PUBLICATIONS

Dittrich et al. (2006) "Micro Total Analysis Systems. Latest Advancements and Trends." Analytical Chemistry 78(12): 3887-3908.

Foleyet al. (2007) "Concentration Gradient Immunoassay. 2. Computational Modeling for Analysis and Optimization." Analytical Chemistry 79(10):3549-3553 (NIH Manuscript 12pp).

(Continued)

*Primary Examiner*—Unsu Jung
*Assistant Examiner*—Leon Y. Lum
(74) *Attorney, Agent, or Firm*—Karen S. Canady; Canady + Lortz LLP

(57) ABSTRACT

Disclosed is a microfluidic assay system and methods that apply flow injection analysis to permit dispersion monitoring. A solution containing a reagent that binds an analyte and a tracer is delivered via pressure-driven flow into the receiving end of the injection channel of the system of the invention. A sample fluid suspected of containing the analyte is delivered into the upstream end of the input channel under conditions permitting flow of the sample fluid toward the downstream end of the assay channel and permitting dispersion of the reagent into the sample fluid. The amount of tracer present in the fluid as it passes over the reference region and the capture region and the amount of binding between the analyte and the capture region are detected. The amount of binding detected between the analyte and the capture region is correlated to the amount of tracer detected in the reference region.

20 Claims, 14 Drawing Sheets

U.S. PATENT DOCUMENTS

| | | | |
|---|---|---|---|
| 5,716,852 A | 2/1998 | Yager et al. | |
| 5,972,710 A | 10/1999 | Weigl et al. | |
| 6,211,956 B1 * | 4/2001 | Nicoli | 356/337 |
| 6,221,677 B1 | 4/2001 | Wu et al. | |
| 6,326,612 B1 * | 12/2001 | Elkind et al. | 250/239 |
| 6,615,856 B2 * | 9/2003 | McNeely et al. | 137/14 |
| 2004/0256230 A1 | 12/2004 | Yager et al. | |
| 2008/0014575 A1 | 1/2008 | Nelson | |

OTHER PUBLICATIONS

Nelson et al. (2007) "Concentration Gradient Immunoassay. 1. An Immunoassay Based on Interdiffusion . . . Microchannel." Analytical Chemistry 79(10):3542-3548(NIH Manuscript 27pp).

Yager et al. (2006) "Microfluidic diagnostic technologies for global public health." Nature 442(7101): 412-418.

Zimmermann et al. (2005) "Modeling and optimization of high-sensitivity, low-volume microfluidic-based surface immunoassays." Biomedical Microdevices 7(2): 99-110.

* cited by examiner

MICROFLUIDIC ASSAY SYSTEM WITH DISPERSION MONITORING

This application claims the benefit of U.S. provisional patent application No. 60/971,463, filed Sep. 11, 2007, the entire contents of which are incorporated herein by reference.

STATEMENT REGARDING FEDERALLY SPONSORED RESEARCH

This invention was made with government support under grant number 5U01 DE014971-05 awarded by the National Institutes of Health. The government has certain rights in the invention.

TECHNICAL FIELD OF THE INVENTION

This invention relates generally to methods and devices using dispersion monitoring to improve the quality and reliability of quantitative assays performed in a microfluidic environment. The invention allows the benefits of dispersion within fluidic samples that create mixing of analytes and reagents while reducing or correcting sources of error that result from dispersion.

BACKGROUND OF THE INVENTION

Developments in microfluidic technology and micro-total analytical systems (microTAS) have proceeded rapidly over the past two decades (Auroux, et al. 2002, Analytical Chemistry 74(12): 2637-2652; Reyes, et al. 2002, Analytical Chemistry 74(12); 2623-2636; Dittrich, et al. 2006, Analytical Chemistry 78(12); 3887-3908). Microfluidic technology promises to have major and far-reaching impact on analytical testing, environmental monitoring, biodefense, and health care. One area that is receiving special focus by many researchers and investors is the development of microfluidic-based point-of-care diagnostic systems (Yager, et al. 2006, Nature 442(7101); 412-418). Due to small sample and reagent requirements, laminar fluid flow, and speed, microfluidic devices can drastically reduce the cost, inconvenience, and time required to analyze a patient sample.

Many researchers who publish for the microfluidic and point-of-care diagnostics literature seem to choose relatively simple assay designs designed solely to demonstrate the function of a novel device they have constructed. These assays are often demonstrated using model systems, meaning the assays are conducted in very simple matrices (such as defined buffer solutions that contain no interferents). Rarely are real patient samples used that have independently been verified to contain the concentration of analyte measured by the new device. A detailed literature is available that describes the processes that govern the outcome of these common assay methods, and it has shown that the physical and chemical processes that underlie these methods are, in fact, anything but simple (Lionello, et al. 2005, Lab on a Chip 5: 254-260, and 1096-1103; Zimmermann, et al. 2005, Biomedical Microdevices 7(2): 99-110, Gervias, et al. 2006, Lab on a Chip 6: 500-507; Gervias and Jensen 2006, Chemical Engineering Science 61: 1102-1121).

The vast majority of biosensors in use or under development rely on the binding of a molecule to an activated surface, and many provide data on the kinetics of binding that are interpreted to obtain quantitative information, such as the concentration of the binding (or competing) species of interest present in the original sample. Until recently, most biosensors have used single-point or spectroscopic detectors (i.e., sensors that produce scalar or vector data, also referred to as zeroth-order or first-order data, respectively). Developments in analytical instrumentation, particularly those that focus on the ability to image biosensor surfaces, have opened up whole new dimensions of potential assay data (literally, simply by adding in an orthogonal spatial index). Therefore, these analytical instruments present researchers and clinicians with powerful new opportunities to obtain subtle analytical information, such as simultaneous multi-species detection, background correction, and run-time calibration, and to do so within minutes rather than the hours typically required for presently used methods. The development of microfluidic assays that exploit these additional dimensions to provide additional quantitative data, not to mention the theories necessary to take advantage of this data, is in its infancy.

Regardless of the format of the assay, in order to make quantitative measurements that represent the true value of the analyte(s) in an unknown, it is essential that the volumes, concentrations and times of interaction of chemical species in the assay system be known to high precision. In contrast to traditional formats, such as those that use a 96-well plate in which the reacting species are provided with lengthy time periods to interact, and that typically provide scalar measurements regarding assay outcomes (e.g., OD), microfluidic assays are often conducted far from equilibrium end-points and can be highly dependent on the small-scale differences in solute concentrations and fluid flow rates, both in space and/or time (Foley, et al. 2007, Analytical Chemistry, 79(10): 3549-3553; Nelson, et al. 2007, Analytical Chemistry, 79(10): 3542-3548).

It is well known that solutes in dissimilar fluids disperse amongst the fluids under the influence of differential velocity fields (such as in fluids in ducts experiencing pressure-driven flow), which leads to solute concentration gradients in the fluids that vary with space and time. Analytical solutions to the concentration of solutes moving in dissimilar fluids under laminar, pressure driven flow were reported by Taylor and Aris in the 1950s (Taylor 1953, Proc. Royal Soc. London. Series A, Mathematical and Physical Sciences 219(1137): 186-203; Taylor 1954, Proc. Royal Soc. London. Series A, Mathematical and Physical Sciences 225(1163): 473-477; Aris 1956, Proc. Royal Soc. London. Series A, Mathematical and Physical Sciences 235(1200): 67-77, Aris 1959, Proc. Royal Soc. London. Series A, Mathematical and Physical Sciences 252(1271): 538-550). However, absent the development of resource-intensive computational models to predict the dispersion behavior of arbitrary channel geometries, it is difficult (if not impossible) to predict the dispersion profile of a given device. This is particularly true when that device is susceptible to random errors during use, such as variations in device geometry due to errors in manufacturing, the presence or appearance of bubbles, and the like. Nevertheless, the dispersion characteristics of a device may have a strong influence on the outcome of a flow-based assay, since the concentration of species near a biosensor surface will be determined not only by the concentration of analyte in the original sample but on the diluting and redistributing effects of dispersion, particularly at early times after introduction of sample or reagent, which occurs when the assay outcome is measured as rapidly as possible, almost always far from thermodynamic equilibrium. Therefore, in order to accurately correlate a given sensor signal to an analytical measurement, or preferably to take advantage of the dynamic yet reproducible processes that occur in microfluidic assays, it is vital to have detailed information regarding the spatiotemporal concentration and flow rate profiles of the fluids above the biosensor surface. To date, this information has been particularly difficult to obtain, often requiring complex or imprecise instrumentation. Either that, or these controlling processes have simply been neglected, possibly to the detriment of the ability to make valid, accurate, and reproducible measurements.

Ruzicka and Hansen both mention in their recent editorial publications their puzzlement that microTAS investigators seemingly largely neglected well-proven dispersion principles used in FIA in their analyses (e.g., (Ruzicka 2005, "Flow Injection Analysis", (3rd ed.) Self-published CD-ROM)). It is noteworthy that Ruzicka and Hansen also recently argue in favor of larger fluidic cross-sections (i.e., diameters>1 mm) in the design their analytical instruments, and write that micro and nanofluidics may not find widespread application after all, due to potential failures due to obstructions and the requirement for high pressures to drive fluid flow through narrow channels (Ruzicka and Hansen 2000, Analytical Chemistry 72(5): 212A-217A; Hansen and Miro 2007, Trends in Analytical Chemistry 26(1): 18-26). On the other side of the FIA/microTAS coin, it is interesting to note that Manz et al. scarcely mention the use of FIA in recent reviews of the state of the art of MicroTAS technology (Auroux, et al. 2002, supra; Reyes, et al. 2002, supra; Dittrich, et al. 2006, supra). And yet it has been shown in many cases to be feasible to implement FIA using microfluidic devices (Leach, et al. 2003, Analytical Chemistry 75(4): 967-972). Moreover, recent perspectives suggest a fertile overlap between microfluidics and FIA (Smith and Hinson-Smith 2002, Analytical Chemistry 74(13): 385A-388A).

Ruzicka writes recently that the lack of broad adoption of FIA into microTAS may be because of the difficulty in machining high-precision valves required for high precision FIA experiments (Ruzicka and Hansen 2000, supra; Ruzicka 2005, supra). As of 2002, for example, commercially available FIA instruments have been priced at several tens of thousands of dollars (Smith and Hinson-Smith 2002, supra). Apparently, the current view about FIA instrumentation seems to be that they must provide highly precise timing and reproducible dispersion functions in order to utilize FIA principles. This level of precision is currently difficult to achieve using low-cost or disposable microfluidic devices, particularly those that utilize commonly available methods for flow control (such as micromachined valves, stepper motor controlled syringe pumps and valves, and as opposed to electrokinetic flow).

For reusable analytical devices, it is often possible to calibrate their operation in advance of measurement using known reference materials. However, it would be truly a leap forward toward the goal of rapid, point-of-care diagnostic testing to develop the ability to monitor and calibrate each disposable device individually and at run-time, in such a way as to correct for errors in solute concentration produced by dispersion. The device and method described herein describes a general method for doing so. While the example presented here uses a flat sensor with surface-sensitive detection, the methods could potentially be extended to other sensor geometries and detection methods.

SUMMARY OF THE INVENTION

The invention provides a microfluidic assay system and methods that incorporate principles of flow injection analysis. Since the concentration of solutes within microfluidic assay devices may be very sensitive to dispersion effects, the accuracy of quantitative determinations using microfluidic devices is limited. The methods permit dispersion monitoring to improve the quality and reliability of data by reducing or correcting sources of error. The contents of a fluidic stream can be compared to a baseline as it flows over a detector array. This permits monitoring of the flow rate, flow pattern, and solute distribution and concentration. This allows the kinetics of binding between two species (usually one in solution and the other on a biosensor surface) to be correlated to the actual rather than assumed relative concentrations of each species. This further provides for controlled mixing between reagent and sample, which can be difficult to achieve in microfluidic devices operating at low Reynold's number. The invention thus provides methods for analyte detection in a microfluidic device without requiring efforts and modifications designed to avoid mass transport limitations, such as using large quantities of sample to avoid errors that arise from solute depletion to the binding surface.

The system comprises an input channel having an upstream end and a downstream end; and an injection channel that intersects with the input channel between the upstream end and the downstream end of the input channel, wherein the injection channel has a receiving end and a terminus disposed at opposing sides of the intersection with the input channel. The system further comprises an assay channel having an upstream end, a downstream end, and a surface that receives fluid flowing from the downstream end of the input channel toward the downstream end of the assay channel.

A capture region is disposed on the surface of the assay channel and provides a surface to which an analyte or reagent dispersed in a fluid sample flowing over the assay channel binds. In one embodiment, the capture region comprises immobilized analyte (or analog thereof) to which the reagent binds. With increasing analyte present in the sample, less reagent is available to bind the capture region. In another embodiment, the capture region comprises immobilized antibody that binds the analyte. With increasing analyte present in the sample, more analyte binds the capture region, bring more reagent (bound to the analyte) to the capture region.

The analyte (or reagent to which the analyte binds) is thus immobilized onto the capture region in such a way that the rate of binding is a function both of its concentration immediately adjacent to the binding surface and the fluid flow properties in the channel (i.e., under conditions of mass transport limitation). The amount of analyte present can be determined in a variety of ways. In one embodiment, the analyte binds to the capture region. In another embodiment, the analyte first binds to a reagent, which reagent then binds, or is prevented from binding, to the capture region.

In addition, a reference region is disposed on the surface of the assay channel. In one embodiment, the reference region is disposed between the input channel and the capture region. In another embodiment, the reference region is downstream of the capture region. In some embodiments, the reference region is at least partially co-extensive with the capture region. The system further comprises detection means for detecting an amount of binding between an analyte and the capture region and for detecting an amount of a tracer present in the reference region, and analysis means in communication with the detection means that correlates the amount of binding detected between the analyte and the capture region to the amount of tracer detected in the reference region.

A fluidic sample is introduced into the system via the input channel, whereby the sample flows from the upstream end toward the downstream end, and into the assay channel. The injection channel is used to introduce a reagent and a tracer. In one embodiment, the system further comprises a pressure-driven flow means for delivering a solution into the injection channel. Examples of pressure-driven flow means include, but are not limited to, a pump, gravitational pressure, bubbling, or capillary forces. In one embodiment, the pump comprises a programmable syringe pump.

As the reagent is dispersed into the sample it interacts with analyte, permitting specific detection of analyte present in the assay channel. The tracer permits monitoring of dispersion of the injected reagent in the assay channel. A preferred tracer has similar diffusivity or molecular weight to the reagents giving it similar dispersion properties for optimal monitoring. The tracer can be co-injected with the reagent as a separate molecule, or it can be conjugated to the reagent. In this embodiment the tracer is inert, binding neither the capture region or interacting in a substantive way with the reagent. Its main purpose is to flow with the reagent such that the concentration and distribution of reagent can be determined.

The tracer is a compound primarily selected for its particular diffusion property and which can be sensitively detected by the array. It is preferable to have an array output that varies linearly with the concentration of the tracer compound at (or near) the array surface. Alternatively, non-surface selective monitoring of tracer concentration is possible. The diffusivity of the tracer compound may be selected to be more or less similar to other soluble elements in the channel. For example, the diffusivity of the tracer may be selected to be similar to the diffusivity of an analyte suspected of being present in a sample. Alternatively, a tracer compound may be selected to more closely match the diffusivity of a reagent used in the analysis. In either case, by monitoring the distribution of the tracer, the distribution (concentration) of soluble compounds of similar diffusivity may be deduced. Further, because the tracer is dispersing through the sample fluid, the concentration of the sample fluid in the vicinity of the tracer may also be deduced (it is the inverse of the tracer concentration). And by measuring the dispersion of both analyte and reagent as generated by a given device (either serially or with multiple distinguishable tracers), the extent of interaction between them may further be deduced, information that may be used to refine the analysis. Quantitative determinations of analyte are based on monitoring, via the tracer compound, the actual concentration of a reagent at the reactive surface, calibrated to the known initial reagent and tracer concentrations. The array response to varying relative concentrations of tracer may be calibrated to the known initial concentration of tracer by flooding the assay channel with the tracer solution and recording the array response.

The analyte, when present in the fluidic sample, binds the reagent. The analyte, bound to the reagent, then either becomes immobilized at the capture region or competes for reagent binding to the capture region, permitting detection of the analyte. In some embodiments, the reagent is an antibody. The reagent can optionally be labeled with a detectable marker. In this embodiment the tracer is inert, neither binding the capture region nor interacting in a substantive way with the reagent. Its main purpose is to flow with the reagent such that the concentration and distribution of reagent can be determined.

In some embodiments, the injection channel is orthogonal to the input channel. In some embodiments, the assay channel is at least twice as wide as the input channel. The system of the invention can optionally further comprise ports that permit fluid flow therethrough when open. The ports can be used to control delivery of fluid into the channels. In one embodiment, the system comprises four ports, wherein a port is located at each of the following: at the upstream end of the input channel, at the receiving end of the injection channel, at the terminus of the injection channel, and at the downstream end of the assay channel.

The system can further comprise, in some embodiments, a reagent channel and a dilution channel, each having an upstream end and a downstream end, in communication with the injection channel, wherein the dilution channel is in series with and between the reagent channel and the injection channel. Including an additional channel between the reagent channel, where reagent is loaded, and the injection channel permits a series of reagent dilutions over a plurality of pulse injections. In one embodiment the system comprises five ports, located at each of the following: at the upstream end of the reagent channel, between the reagent channel and the dilution channel, at the upstream end of the input channel, at the terminus of the injection channel, and at the downstream end of the assay channel.

In one embodiment, the device is filled to improve operation. The dilution channel is filled with a buffer solution that contains neither reagent nor sample. This may be accomplished by injecting a buffer solution into the port located at the downstream end of the assay channel while closing the port at the upstream end of the reagent channel. Excess fluid will exit from the port between the reagent channel and the dilution channel. Once these channels are filled, reagent is injected into the port at the upstream end of the reagent channel, leaving the port at the downstream end of the assay channel closed. This will cause the excess reagent to exit the port between the reagent channel and the dilution channel, establishing a sharp boundary between the reagent fluid and the buffer fluid. The port between the reagent channel and the dilution channel is then closed so that reagent solution may be dispersed into the buffer-filled dilution channel. Optionally, the assay channel may then be filled with sample prior to the onset of reagent injections without substantially disturbing the fluidic arrangement between the reagent and buffer. Optionally, the buffer solution in the dilution channel may be replaced with another fluid that reacts with the reagent prior to reacting with the analyte or biosensor surface.

Also provided by the invention is a method of detecting an analyte in a sample. The method comprises delivering via pressure-driven flow a solution containing a reagent that binds the analyte and a tracer into the receiving end of the injection channel of the system of the invention. The method further comprises delivering a sample fluid suspected of containing the analyte into the upstream end of the input channel under conditions permitting flow of the sample fluid toward the downstream end of the assay channel and permitting dispersion of the reagent into the sample fluid, wherein the analyte, if present, alters binding of the reagent to the capture region, such as by reducing the binding of reagent to the capture region via competition. The method further comprises detecting the amount of tracer present in the fluid as it passes over the reference region and the capture region; and detecting the amount of binding between the reagent and the capture region. The amount of binding detected between the reagent and the capture region is correlated to the amount of tracer detected in the reference region.

In one embodiment, the method is performed without use of electrokinetic flow. Electrokinetic flow is typically used in prior art methods to eliminate dispersion, whereas the present system obviates this need. Instead, a plug of reagent can be injected or delivered with pressure-driven flow, leading to Taylor dispersion of the reagent into the sample. This produces inverse gradients of reagent and sample concentration around the reagent pulse, as in flow injection analysis systems. In some embodiments, the delivering via pressure-driven flow comprises use of a pump, gravitational pressure, bubbling, or capillary forces. In a typical embodiment, the pump comprises a programmable syringe pumps.

The detecting comprises surface plasmon resonance (SPR) in a typical embodiment. Alternatively, the detecting can comprise colorimetry or fluorescence detection. In addition, the delivering step can be modulated by use of ports disposed at each of the receiving end and the terminus of the injection channel. In one embodiment, the delivering is modulated by closing the ports upon filling of the injection channel with the solution. Additional ports and channels can be used in the method, as described above for the system.

BRIEF DESCRIPTION OF THE DRAWINGS

FIG. 1A shows the layers separately, while FIG. 1B shows the layers collapsed together to form the device.

FIG. 7B shows a difference image of the functionalized surface following exposure to a number of antibody-containing pulses represented by the one shown in FIG. 7A.

FIG. 8A corresponds to the period between frame numbers ~60 and ~150. FIG. 8B is representative of the pulses generated during frame numbers >150. As discussed, errors in sample injection sequencing and solute distribution may be monitored and corrected for using this method.

FIG. 10A: The principal device geometry consists of a set of crossed channels 32, 34 connected via a narrow neck at the injection tee 30 that widens into a main channel 14. A reactive surface (binding surface 38) may be patterned across this main ("assay") channel 14, with all other surfaces rendered inert (e.g., with PEG or BSA), including the reference surface 36.). Flow through three of the four ports 42, 44, 46, 48 is controlled using positive displacement pumps; the fourth is left open. FIG. 10B: A two-step flow sequence is used for pulse loading and injection: 1. Reagent solution containing a tracer compound is simultaneously pushed into the top port 42 while pulling fluid from the waste line 44 directly downstream. 2. Once this channel 34 is filled, flow is stopped and the plug of reagent is pushed into the (orthogonal) assay channel 14 using the sample fluid. Convection and diffusion cause reagent to disperse into the sample. The area to be imaged 40 is indicated with dashed box. FIG. 10C: Three consecutive SPR difference images of a pulse of reagent (a buffered solution of antibody with dextrose as a refractive index tracer) flowing through the main channel over a binding region. The tracer distribution corresponds to the concentration and distribution of reagent in the sample fluid. FIG. 10D: Shape and relative dilution of water (top) and dextrose (bottom) pulses. Smooth lines are Gaussian fits. Data obtained from separate but identical device geometries and operating conditions. Dextrose in pulse mirrors sample dilution (water pulse), as expected.

DETAILED DESCRIPTION OF THE INVENTION

Overview

Figures 1A, 1B:
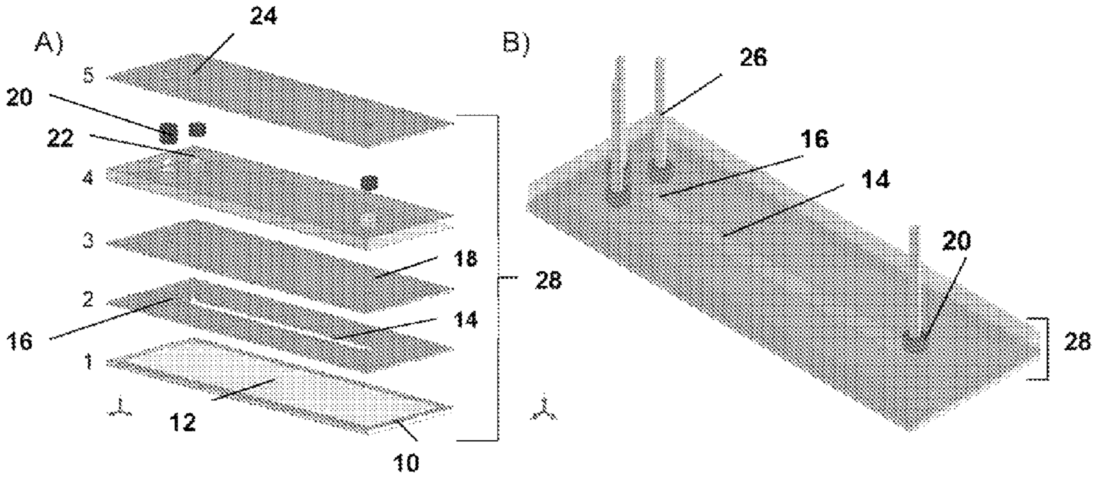
FIGS. 1A-1B. Schematic illustration of polymeric laminate disposable microfluidic device

The invention overcomes the problems encountered in microfluidic assay devices with regard to uneven solute distribution within the channels of the device. Rather than modify the devices and methods to strive for perfectly-designed devices and delivery of ideal boluses, the methods of the invention apply flow injection analysis to a microfluidic assay device. The methods permit dispersion monitoring to improve the quality and reliability of data by reducing or correcting sources of error. The contents of a fluidic stream can be compared to a baseline as it flows over a detector array. This permits monitoring of the kinetics of binding, flow rate, flow pattern, and solute distribution and concentration. The invention thus provides methods for analyte detection in a microfluidic device without requiring efforts and modifications designed to avoid mass transport limitations, such as using large quantities of sample to accelerate flow. The invention obviates the need for electrokinetic flow and other expensive techniques designed to achieve ideal uniform flow and dispersion.

The invention features a number of advantages. First, the dispersion of solutes within solutions flowing in microfluidic devices are monitored using imaging techniques, thereby enabling FIA methods to be exploited on low-cost, single-use microfluidic devices that have relatively low precision manufacturing requirements. The ability to monitor actual solute dispersion in real-time enables more precise quantitation by enabling the device to correct for performance errors that would otherwise be propagated into the error in the measured value. Second, two-dimensional spatial data can be obtained regarding the dispersion function, rather than detected in one dimension, as is the case for most other FIA systems. Third, the imaging of the two-dimensional dispersion function is surface sensitive in this case (though not necessarily), and therefore is more relevant to the processes that occur near a biosensor surface at which binding relevant to quantitative assay outcomes takes place.

Fourth, the dispersion function is monitored for any given device, rather than requiring that a dispersion function for a specific device design is predictable under most any operating condition. This enables the use of devices that may or may not produce regularly shaped pulses (i.e., geometrically simple or readily comparable to basic shapes, such as rectangles). Fifth, the dispersion function is monitored for each pulse using a device that may or may not produce highly reproducible pulses, due to, for example, variations in flow rates during the course of the experiment as a result of using inexpensive pumps with relatively low performance characteristics.

Further, the time, space, concentration, and flow rate-dependent events that may occur at a two-dimensional biosensor surface may be correlated to the two-dimensional dispersion function measured either immediately upstream of the binding area, in a portion of the channel adjacent (transverse relative to the convective flow direction) to the binding area, or immediately downstream of the binding area, or a combination of the three. Correlating this dispersion function involves the patterned distribution of non-binding (monitoring or reference) areas and binding (assay detection or capture region) areas of the surface.

A small amount of a refractophore or other tracer compound may be added to a sample as a contrast agent to enable the visualization of the dispersion function. The refractophore may be an inert compound, or participate in a specific reaction near or at the biosensor area. This refractophore may be added in a known proportion to the reactive compounds otherwise participating in the reaction used to make quantitative measurements using the biosensor, thereby enabling the monitoring of concentrations of the reactive compounds participating in the detection/quantitation process.

Finally, the observation of errors in the uniformity or reproducibility of the dispersion function may be used to detect and/or correct for errors or disturbances in the flow uniformity as may be caused by, for example, the presence of flow obstructions (such as small or large bubbles, grit, or the pressure-induced deformation of the flow channel).

DEFINITIONS

All scientific and technical terms used in this application have meanings commonly used in the art unless otherwise specified. As used in this application, the following words or phrases have the meanings specified.

As used herein, "pressure-driven flow" means a non-uniform velocity field. This can be achieved, for example, by positive displacement pumping, gravity, bubbling, or capillary forces.

As used herein, "port" means a movable part that can be opened or closed. When opened, the port allows fluid to pass through; when closed, the passage of fluid is substantially reduced.

As used herein, an "analyte analog" means a molecule that is capable of binding a binding partner, such as an antibody, with the same specificity as the analyte itself. This can include the analyte as well as sufficiently similar molecules.

As used herein, a "plurality" means more than one of the indicated material. This can include more than one member of the indicated class of material, or more than one of the same member of the indicated class of material. For example, a plurality of reagents can refer to both heterogeneous and homogeneous populations of reagents.

As used herein, "a" or "an" means at least one, unless clearly indicated otherwise.

System and Device for Dispersion Monitoring

The invention provides a microfluidic assay system. The system comprises an input channel having an upstream end and a downstream end; and an injection channel that intersects with the input channel between the upstream end and the downstream end of the input channel, wherein the injection channel has a receiving end and a terminus disposed at opposing sides of the intersection with the input channel. The system further comprises an assay channel having an upstream end, a downstream end, and a surface that receives fluid flowing from the downstream end of the input channel toward the downstream end of the assay channel. A capture region is disposed on the surface of the assay channel and provides a surface to which an analyte dispersed in a fluid sample flowing over the assay channel binds. The analyte can then be immobilized onto the capture region. In addition, a reference region is disposed on the surface of the assay channel between the input channel and the capture region. In some embodiments, the reference region is at least partially coextensive with the capture region. The system further comprises detection means for detecting an amount of binding between an analyte and the capture region and for detecting an amount of a tracer present in the reference region; and analysis means in communication with the detection means that correlates the amount of binding detected between the analyte and the capture region to the amount of tracer detected in the reference region.

A fluidic sample is introduced into the system via the input channel, whereby the sample flows from the upstream end toward the downstream end, and into the assay channel. The injection channel is used to introduce a reagent and a tracer. In one embodiment, the system further comprises a pressure-driven flow means for delivering a solution into the injection channel. Examples of pressure-driven flow means include, but are not limited to, a pump, gravitational pressure, bubbling, or capillary forces. In one embodiment, the pump comprises a programmable syringe pump.

The reagent interacts with analyte, permitting detection of analyte present in the assay channel. The tracer permits monitoring of dispersion of the injected reagent in the assay channel. A preferred tracer has similar diffusivity or molecular weight to the reagent, giving it similar dispersion properties for optimal monitoring. In one embodiment, the tracer binds to the capture region. The tracer can optionally be conjugated to a molecule that binds the capture region. The tracer can be co-injected with the reagent as a separate molecule, or it can be conjugated to the reagent. The analyte, when present in the fluidic sample, binds the capture region, where it becomes immobilized. Reagent then binds the captured analyte, permitting detection of the analyte. In some embodiments, the reagent is an antibody. The reagent can optionally be labeled with a detectable marker.

In some embodiments, the injection channel is orthogonal to the input channel. In some embodiments, the assay channel is at least twice as wide as the input channel. The system of the invention can optionally further comprise ports that permit fluid flow therethrough when open. The ports can be used to control delivery of fluid into the channels. In one embodiment, the system comprises four ports, wherein a port is located at each of the following: at the upstream end of the input channel, at the receiving end of the injection channel, at the terminus of the injection channel, and at the downstream end of the assay channel.

The system can further comprise, in some embodiments, a reagent channel and a dilution channel, each having an upstream end and a downstream end, in communication with the injection channel, wherein the dilution channel is in series with and between the reagent channel and the injection channel. Including an additional channel between the reagent channel, where reagent is loaded, and the injection channel permits a series of reagent dilutions over a plurality of pulse injections. In one embodiment, the system comprises five ports, located at each of the following: at the upstream end of the reagent channel, between the reagent channel and the dilution channel, at the upstream end of the input channel, at the terminus of the injection channel, and at the downstream end of the assay channel.

SPR Imaging

A suitable method of detection or imaging is based on an optical detection method known as surface plasmon resonance (SPR). This method is well known and widely applied in the biosensor literature. Surface plasmons are surface-bound oscillations of electrons in a metal that may be excited by reflecting light off the metal under specific conditions. Primary among those conditions are the appropriate matching of refractive indices between the metal and the medium directly above it. Most SPR experiments are conducted by first setting the conditions for resonance (under which the reflected light intensity is near minimum), then monitoring the change in reflected intensity that occur as the conditions on the surface change—as a result of the adsorption of molecules from solution, for example. This method is suitable for SPR imaging detection, wherein a single detector is replaced by a CCD (or similar) that provides a picture of the different binding events distributed across the sensor area.

For the purposes of this invention, SPR is particularly appealing due to its surface sensitivity; that is, it detects changes in the refractive index of the medium only in close proximity to the surface (~300 nm, in this case). For the purposes of surface binding assays based on microfluidic flow, only those molecules that have mean diffusion distances on this length scale may be reasonably expected to interact with the sensing surface over the interaction time scales provided for in most microfluidic assay formats. While this surface-sensitive property of SPR greatly facilitates implementation of the method disclosed herein, it is not necessary for its implementation, as other methods are known in the art for selectively monitoring near-surface events or for correlating bulk phenomena to near surface properties.

Surface Patterning

A typical embodiment of the invention provides the ability to prevent (or drastically reduce) surface binding events to the microfluidic channel surface upstream of the sensor surface. A simple, inexpensive, and rapid method for patterning a microfluidic surface can be performed in such a way as to prevent fouling between the device inlets and the sensor area, to enable a sharp, linear transition transverse to the convective (axial) flow direction from the non-fouling region to a functionalized sensor surface that can selectively bind molecules from the solution. This technique allows for any number of different diffusion- or dispersion-based processes to occur prior to having the molecules in the flowing solution interrogated by the sensor surface. This method stands in contrast to the widely used microcontact printing in its economy of reagents and time and suitability for use with a wide variety of solvents.

Briefly, the method uses capillary wetting to fill a small space between a mask and the sensor surface. The mask placed in contact with the substrate restricts the distribution of solutions placed between the mask and substrate by capillary wetting. The masks are typically cut from materials such as Mylar™ or acrylic (PMMA) using a laser-cutting system, though a wide variety of materials could be used. The mask is placed in contact with the substrate (a gold-coated glass microscope slide, in this case), and a small (~15 μL) volume of solution is gently placed in contact with the gold surface such that the liquid begins to wet both surfaces. Capillary forces then cause the liquid to spread across the area of the mask up to its edges. Appropriately carried out (e.g., without depositing an excess of liquid), the solution deposited this way fills only the area under the mask. Molecules in the liquid may thereby bind to the surface underneath the mask, selectively functionalizing the substrate area defined by the mask pattern. Following an adequate incubation period, the mask is carefully removed, and the substrate rinsed with clear solvent such that excess is washed away from virgin substrate. This process may be repeated as many times as necessary to complete the required surface patterning.

In one embodiment, the area of the microfluidic device between the fluidic inlets and a distance downstream is treated with a PEG-terminated alkylthiol dissolved in ethanol. Alkylthiols self-assemble on gold surfaces and PEG-terminated thiols will resist the non-specific adsorption of proteins from solution. In this way, the substrate can be rendered non-fouling within this region. At some distance downstream of the inlets (typically in our case ~20 mm, though the distance is arbitrary), and immediately adjacent to the PEG-functionalized region, the same patterning method can be used to coat the surface with a different molecule designed to specifically bind proteins from solution. The specific chemistry used may be selected from among a very wide variety of choices, but this particular example uses the passive adsorption of a bovine serum albumin (BSA) covalently conjugated with the analyte of interest (phenytoin, in this case) to provide a specific functionality of this area of the sensor surface. Again, this method allows one to rapidly and conveniently provide for a non-fouling surface upstream of a specifically functionalized sensor with an abrupt, orthogonal interface between the two regions.

This method is particularly useful for several reasons: the distance between the fluidic inlets and the sensor surface allows for the full development of fluid velocity transverse to the width of the channel; in some assay formats allows other processes, such as inter-diffusion of solutes between adjacent flow streams, to occur before the result is interrogated by the binding surface; and providing for a non-fouling area within the SPR imaging region upstream of the binding surface enables control, reference, and correction of binding events to events detectable in the non-fouling region.

Microfluidic Device Design and Construction

Microfluidic devices can be constructed out of, amongst the various alternatives, polymeric materials, such as Mylar™ (PET) and acrylic (PMMA), laminated together to form planar microfluidic channels using conventional techniques well-known in the art. FIG. 1 schematically illustrates how these devices 28 are constructed and how the off-card fluid control systems (such as pumps, sample selection valves, and associated tubes 26 and fittings) are connected to the device 28. Those skilled in the art appreciate that numerous variations and alternative designs and modes of construction for microfluidic assay cards and devices are available and known in the art.

Layer 1 of the example shown in FIG. 1 is a gold-coated 12 glass microscope slide 10 patterned as described above. Layer 2 is Mylar (coated on both sides with pressure-sensitive adhesive (PSA)) with channel 14 cut from center. Note, in this embodiment, 3 inlets 16 feed into channel. Layer 3 is Mylar (with PSA on top) defining the top of the microfluidic channel and providing for the retention 18 of o-rings 20 in the next layer. Layer 4 is PMMA o-ring 20 seat 22. Layer 5 is Mylar (with PSA on the bottom), used to retain the o-rings 20 in place 24 in the PMMA layer below. FIG. 1A shows the layers separately, while FIG. 1B shows the layers collapsed together to form the device 28. Depicted are the channel 14, inlets 16, o-rings 20 and tubes 26.

Methods for Dispersion Monitoring and Analyte Detection

The methods of the invention apply flow injection analysis to a microfluidic assay device. The methods permit dispersion monitoring to improve the quality and reliability of data by reducing or correcting sources of error. The contents of a fluidic stream can be compared to a baseline as it flows over a detector array. This permits monitoring of the kinetics of binding, flow rate, flow pattern, and solute distribution and concentration. The invention thus provides methods for analyte detection in a microfluidic device without requiring efforts and modifications designed to avoid mass transport limitations, such as using large quantities of sample to accelerate flow.

The invention provides a method of detecting an analyte in a microfluidic sample. The method comprises delivering via pressure-driven flow a solution containing a reagent that binds the analyte and a tracer into the receiving end of the injection channel of the system of the invention. The method further comprises delivering a sample fluid suspected of containing the analyte into the upstream end of the input channel under conditions permitting flow of the sample fluid toward the downstream end of the assay channel and permitting dispersion of the reagent into the sample fluid, wherein the analyte, if present binds to the capture region. The method further comprises detecting the amount of tracer present in the fluid as it passes over the reference region and the capture region; and detecting the amount of binding between the analyte and the capture region. The amount of binding detected between the analyte and the capture region is correlated to the amount of tracer detected in the reference region.

In one embodiment, the method is performed without use of electrokinetic flow. Electrokinetic flow is typically used in prior art methods to eliminate dispersion, whereas the present system obviates this need. Instead, a plug of reagent can be injected or delivered with pressure-driven flow, leading to Taylor dispersion of the reagent into the sample. This produces inverse gradients of reagent and sample concentration around the reagent pulse, as in flow injection analysis systems. In some embodiments, the delivering via pressure-driven flow comprises use of a pump, gravitational pressure, bubbling, or capillary forces. In a typical embodiment, the pump comprises a programmable syringe pump.

The detecting comprises surface plasmon resonance (SPR) in a typical embodiment. Alternatively, the detecting can comprise colorimetry or fluorescence detection or other known detection method. In addition, the delivering step can be modulated by use of ports disposed at each of the receiving end and the terminus of the injection channel. In one embodiment, the delivering is modulated by closing the ports upon filling of the injection channel with the solution. Additional ports and channels can be used in the method, such as at the upstream end of the input channel and at the downstream end of the assay channel. In addition, for embodiments employing a dilution channel in series with a reagent channel, ports can be used to control dilution and reagent delivery. A reagent channel can be used to load reagent onto the card, or into the input channel of the microfluidic device. A dilution channel added between the reagent channel and the input channel allows preparation of a series of reagent dilutions over a number of pulse injections. The reagent can be loaded into a dry channel to prevent dispersive dilution of the reagent during loading. The remainder of the device is loaded with buffer. Excess fluid, both reagent and buffer, exit a common port, resulting in a sharp boundary between the buffer at the entrance to the dilution channel. After filling of the device, this port is plugged. Further details of port use in the method are exemplified in the examples below.

EXAMPLES

The following examples are presented to illustrate the present invention and to assist one of ordinary skill in making and using the same. The examples are not intended in any way to otherwise limit the scope of the invention.

Example 1

Biosensor Operation

SPR imaging apparatus and the microfluidic devices have traditionally been used to conduct small-molecule immunoassays. Note that while this describes a specific assay format, other formats are compatible with the techniques disclosed herein, such as direct detection (capture molecule on surface, binding event between capture molecule and analyte detected directly), sandwich immunoassay formats, etc. However, since our research is focused on using SPR imaging as the detection methodology, and since our targets of interest are small molecules, and because SPR does not typically have adequate sensitivity to directly detect binding of small molecules, an indirect detection method has been used instead. This has been accomplished by mixing an antibody to the analyte of interest into a buffer solution containing the analyte, then flowing the mixture through the microfluidic device and over the sensor functionalized with an analogue of the analyte. Antibody molecules with at least one unoccupied binding site may bind to the functionalized sensor surface, leading to a readily detectable SPR signal. Specific antibody binding events are measured by measuring a change in the reflected intensity at the SPR detector.

Figure 2:
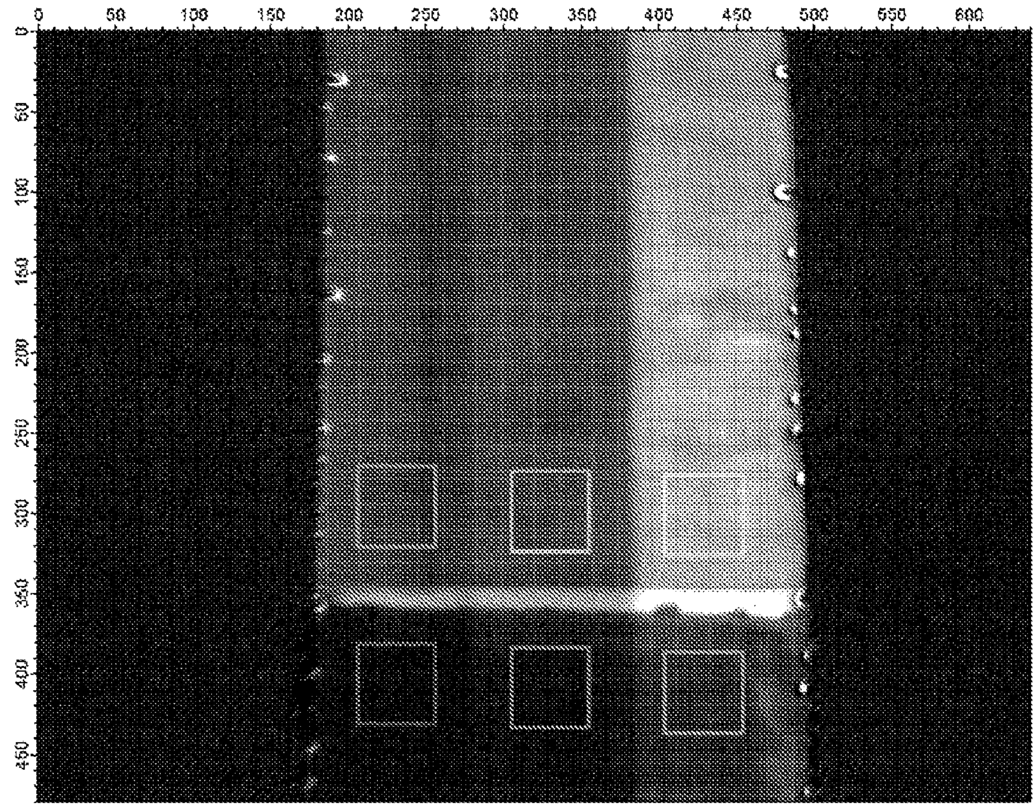
FIG. 2. SPR difference image illustrating principle features of assay data. The fluidic channel occupies the center ~50% of the image. The regions of interest (ROIs) used to calculate the data shown in FIG. 3 are represented in boxes, with the non-fouling area in the lower row of boxes and the binding area in the upper row of boxes.

An example of the experimental data obtained from such an assay is shown in FIG. 2. An SPR image collected before the start of the experiment was subtracted from all subsequent images collected during flow. In this way, only the changes in reflected light intensity are highlighted (recall that changes in reflected intensity may occur either by changes in the refractive index of the bulk medium above the sensor surface or by adsorption of protein molecules to the sensor). The device used in this experiment is illustrated in FIG. 1B with three fluidic inlets converging into a single channel. The ratio of convective to diffusive mass transport is roughly 3000, so that inter-diffusion of molecules between the three flow streams can be safely neglected. Relative to the image in FIG. 2, flow is from bottom to top at a total volumetric flow rate of 300 nL/sec (100 nL/sec/inlet). The channel is 3.6 mm wide in the horizontal direction and ~60 μm deep. The imaging area is split between the PEG-functionalized region (lower ~25% of the image) and the BSA-PHN functionalized area (upper 75%). The squares shown in FIG. 2 represent the regions of interest (ROIs) used to calculate an average intensity value used as a simple metric to evaluate the outcome of the experiment.

Figure 3:
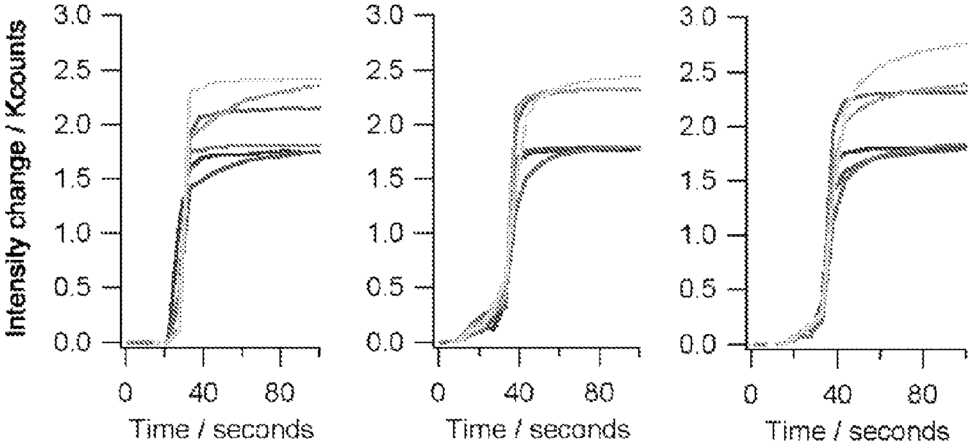
FIG. 3. Example data plot of SPR monitored dispersion profile for the same device connected to flow control system three separate times. Injection of a buffer solution (RI 1.3345) into a device filled with water (RI 1.33300) leads to SPR intensity change that represents the degree of dispersion/concentration of the buffer solution near the sensor surface over time. Ideally, the dispersion function for all three streams would be identical and reproducible enabling a comparison of the binding rates between the three streams, clearly, in this example they are not. Knowledge of the dispersion function would either enable error detection or error correction.

The experiments are conducted by filling the device with an aqueous buffer (such as PBS), then injecting the sample containing the analyte and added antibody. As molecules encounter the sensor region, either changes in the bulk refractive index or surface binding events lead to a change in the reflected intensity at the detector. These changes must be interpreted in some manner fashion that enables the quantitative determination of the analyte in the sample. One such method is to calculate the average intensity of a region in contact a specific flow stream and correlate the rate of intensity change the rates determined using control or calibration experiments, or to compare rates among various flow streams (see FIG. 3). Ideally, this would be all that is necessary to conduct a rapid, quantitative microfluidic assay. In reality, there are many difficulties associated with this method that conspire to the detriment of the reproducibility, accuracy and precision of this approach to a quantitative assay metric. Among the most vexing problem is the fact that the rate of change in the SPR signal is controlled by many factors other than the concentration of unoccupied binding sites, such as unpredictable differences in bulk refractive index between the sample and the carrier fluid, the changing fractional surface coverage of the sensor, disruptions to the fluid flow caused, for instance, by the inclusion or development of a bubble in the microfluidic channel, or unpredictable dispersion functions of the different streams (FIG. 3).

Figure 4A:
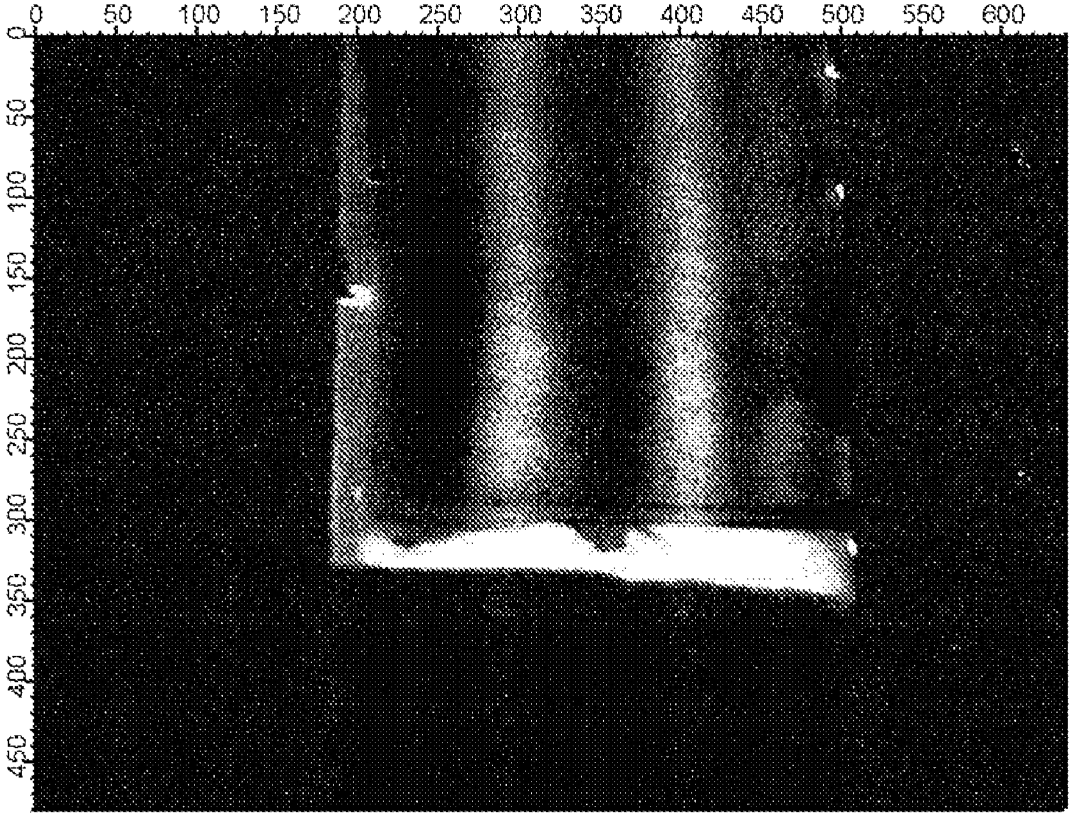
FIGS. 4A-4B. Colorized SPR difference image (4A; white-hot) and ROI plot (4B, colors as in FIG. 3) from indirect competitive assay but where flow was disrupted unexpectedly.
Figure 4B:
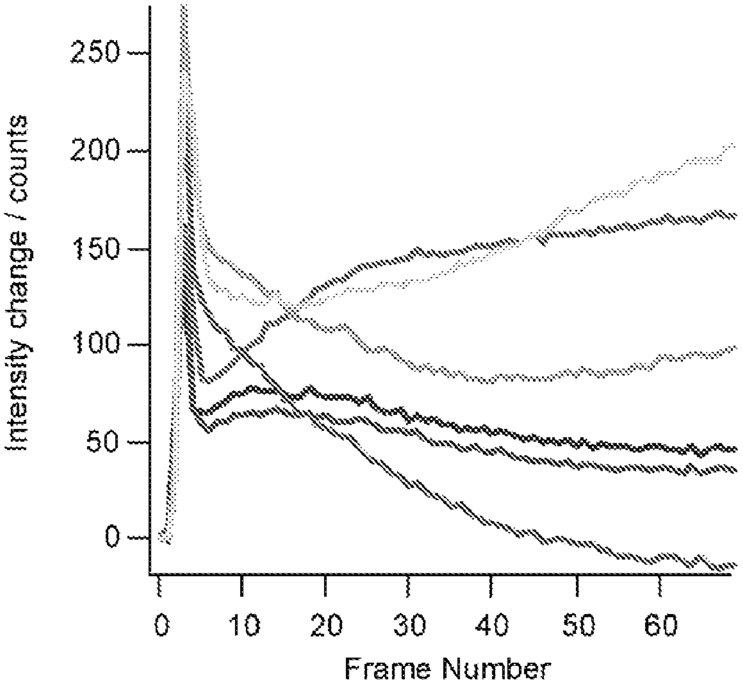

FIGS. 4A-B provide an additional example of what may occur in this assay format. In this case, the expected uniform binding across each stream did not occur, leading to the rate data shown in FIG. 4B. Clearly, this rate data would be difficult to interpret in the best of circumstances. The image data shown in FIG. 4A does not clearly indicate possible reasons for the unexpected results. In any event, it is clear that such flow disruptions or unexpected behavior in a device that aims to provide quantitative information for the purposes of making clinical diagnostics or changes to therapeutic regimens adds significant risk to their use.

There are a number of additional factors that may be anticipated in the use of a disposable polymeric device that would contribute to significant uncertainties in flow rate, solute concentrations, and solute distribution within flows in a microfluidic channel. For instance, for those devices that use a dry reagent storage depot on card to deliver the necessary assay components, accurate knowledge of the concentration and activity of these reagents is essential. Difficulties in manufacturing inexpensive yet precise micro/nanoliter valves on a disposable device may also lead to substantial uncertainties in the volumes of fluids delivered to a sensor surface. These and other unexpected problems could cause significant risk to a patient who is relying such devices to provide valid, reliable quantitative assay data, and therefore pose substantial obstacles to the development of useful, inexpensive point-of-care diagnostic instruments in the near future. What follows is a description of a novel method that takes advantage of a simple concept to enable the monitoring of all these factors and thereby dramatically reduces the risks associated with conducting quantitative assays using microfluidic devices.

The concepts presented below are familiar concepts of Flow Injection Analysis (FIA; see Ruzick and Hansen, 1988, Flow Injection Analysis (New York: Wiley & Sons; Fresenius, 1988, Anal. Chem. 329:653-677). FIA systems, however, have been specifically designed such that the dispersion functions generated by the equipment are precise and reproducible. In fact, reports describing FIA carried out using microfluidic systems have reported dispersion functions (as measured, for example, by peak area or peak height) with RSD % at around 2% for a specific device manufactured in glass (in contrast, high precision, non-microfluidic FIA systems have RSD of dispersion functions much lower, perhaps on the order of 0.5%). It is possible, if not likely, that polymeric microfluidic devices, with untrained user operated fluidic connections to off-card devices, may have even poorer reproducibility. Naturally, low precision dispersion functions, whether analyzed using the techniques of FIA or using stopped flow or continuous flow necessarily reduce the precision of a quantitative measurement. There are several key differences: to the best of our knowledge, the dispersion of each sample zone (to use FIA terminology) has never before been imaged, nor has detection of dispersion occurred at run-time, immediately prior to contact with a sensor surface, and again, to the best of our knowledge, this is the first instance of the use of a device that produce relatively low-precision dispersion function, but that the actual dispersion produced by each injection is imaged, and the data used to interpret the sensor response to the sample zone produced.

Example 2

Pulsed Sample Injection

A simple microfluidic device layout that enables the generation of a bolus or pulse of a sample and the delivery of that pulse into a channel that is previously filled with a carrier solution involves injection of sample at the upstream end. By adding a small amount of salt (or some other substance that changes the refractive index of the sample relative to the carrier fluid) via an orthogonal injection channel, SPR provides the ability to readily monitor the location and distribution of the pulse as it traverses the imaging area. By dividing the detector area into non-binding and binding areas, and by including a molecule in the sample that will specifically adsorb to the binding area, it is possible to monitor the accumulation of the adsorbate and correlate that to the distribution and other properties of each sample pulse.

The lower (upstream) two-thirds of the channel surface have been treated with a PEG-terminated thiol, while the upper third of the channel surface is coated with a specific binding functionality (BSA-phenytoin conjugate, in this case). Pulses of antibody solution are flowed through the channel, resulting in the detectable accumulation of antibody to the binding area. A fairly uniform distribution of intensity throughout the pulse is observed, except near the walls of the channel. A similar uniformity of accumulated antibody to the binding surface is found in the capture region.

Example 3

Assay Calibration for Quantitative Analysis

Device calibration is essential for a point-of-care diagnostic instrument to provide valid quantitative data. Precise and accurate knowledge of fluid volumes delivered across the sensor surface, solute concentrations, flow rates, solute distribution within and across the channel and dispersion factors is required for quantitating an assay. Solutions with added standards and controls for surface fouling and other effects may also be needed. This latter point is one of the important rationales for having separate fluid inlets into a common channel, that is, to provide for run-time controls and calibrants necessary for quantitative determination. Implementing such controls imposes a strict condition on the ability to make valid comparisons among the sensor responses in each separate stream.

Example 4

Correlation Between Refractive Index and Concentration

Figure 5:
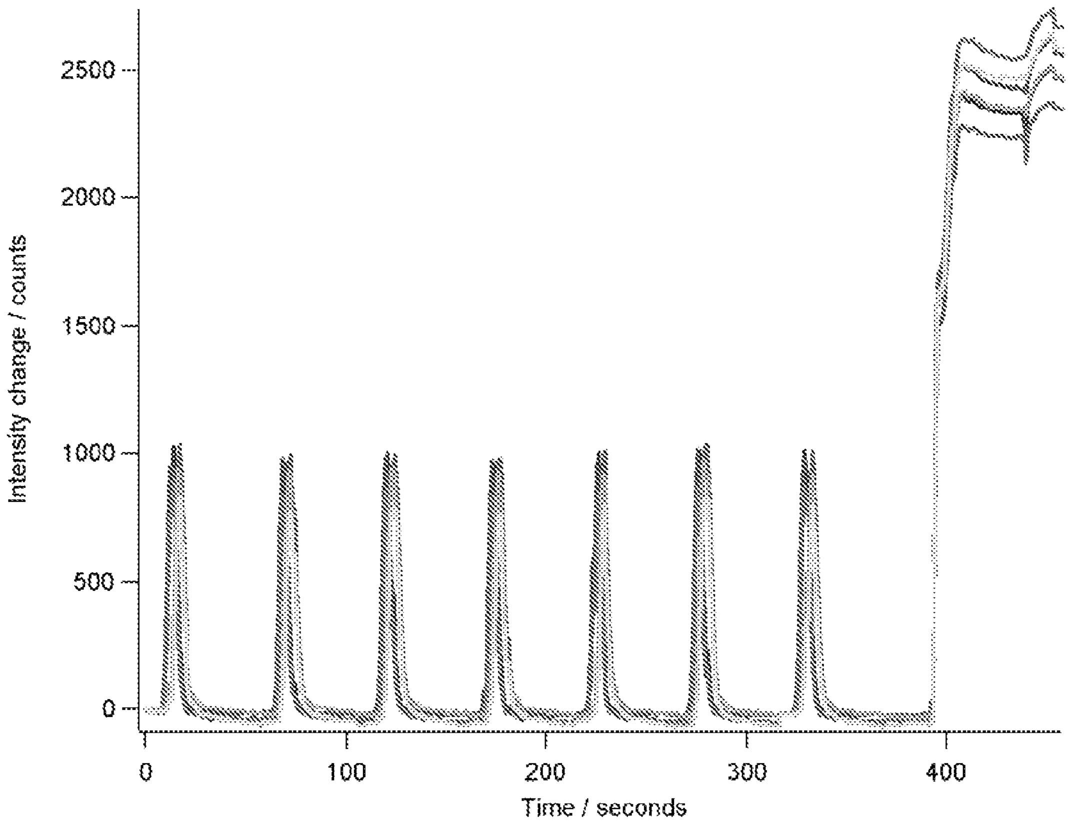
FIG. 5. ROI intensity vs. time plot for seven consecutive sample pluses followed by continuous sample injection.

The concentration of binding species near a sensor surface will have a strong impact on the rate and amount of adsorbate. Therefore, knowledge of the concentration of binding species is critical for conducting quantitative assays. FIG. 5 illustrates how the concentration of a solute in the pulse can be monitored. As shown in FIG. 5, injection of a continuous stream of the sample solution eventually leads to a steady-state concentration of sample over the detector, at which time the intensity resulting from the undiluted sample is determined. Comparison between pulse peak intensity and peak intensity obtained during continuous flow of solution enables determination of relative concentration of pulses, provided that the detector response over the intensity range is known. This method can be extended to monitor or calculate the concentration of a binding species in the pulsed sample, if the binding species is different from the solute added to image the pulse, if the relative concentrations of the two species are known.

It is worth noting that while conventional FIA averages the signal resulting from the dispersion of solute throughout the entire channel, this surface-sensitive detection mode, while not necessary, provides information regarding the concentration of species very near the sensor surface, where most, if not all, relevant mass transport processes occur in this or equivalent assay formats.

Example 5

Correlating Sample Injection to Surface Binding

Figure 6:
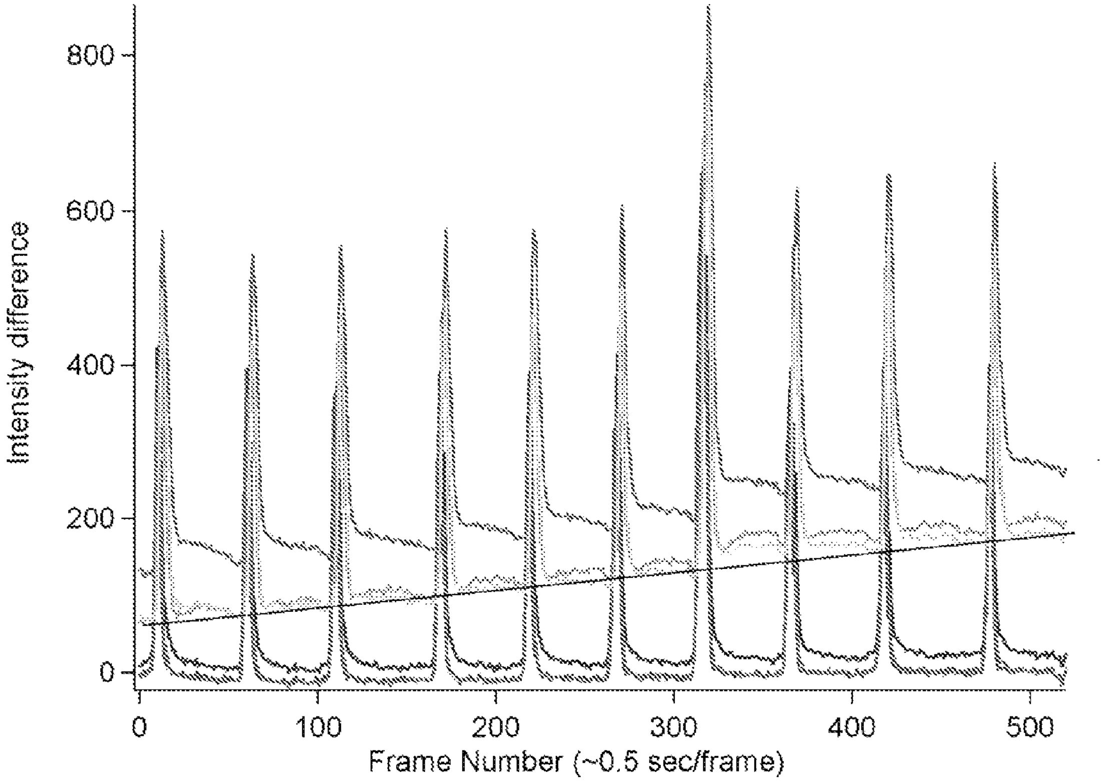
FIG. 6. ROI intensity vs. time plot demonstrating correlation between peak area and surface accumulation.

As shown in FIG. 6, an ROI intensity versus time plot demonstrates the correlation between peak area and surface accumulation. The lower traces show the intensity vs. time data (1 second/frame) for ten consecutive samples traversing the PEG (non-fouling, or reference) region of a device, whereas the upper traces show the same series of pulses traversing over the BSA-phenytoin (binding, or capture) region of the sensor. Note the excellent correlation of the peak heights obtained from each pulse. Note also that the upper traces do not return to their baseline value, but rather the average intensity for those ROIs steadily increases. This is due to the accumulation of antibody present in the sample pulses to the binding area of the sensor, but not to the non-fouling areas. Note also the significantly larger peak height of the seventh pulse (t~310), and the corresponding additional increase in surface coverage. The amount of adsorbate can thus be directly correlated to the volume (via pulse area) and concentration (via pulse intensity) of binding species in the sample, greatly facilitating precise quantitative determination of analyte in this assay format.

Example 6

Error Detection

Figure 7A:
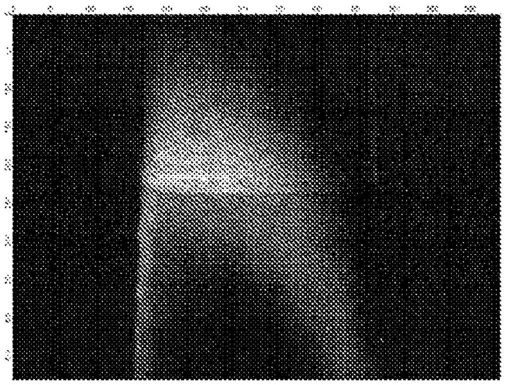
FIGS. 7A-7B. Indicator pulse (7A) and surface pattern (7B) demonstrating ability to detect and potentially correct for flow disruptions. The pulse shown in FIG. 7A was imaged within a device that had a large gas bubble between the fluid inlets and the imaging area.
Figure 7B:
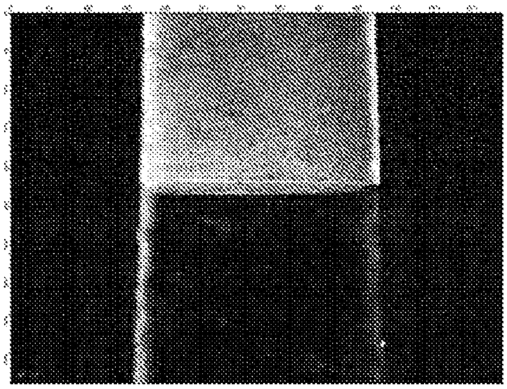

Among the greatest risks in deploying a disposable device for quantitative determinations used for patient diagnosis or therapeutic monitoring is the failure of the device due to disturbances in flow (caused, for instance, by grit, bubbles, valve or pump errors or failure). Detecting such failures are necessary to ensure patient safety and widespread acceptance of the diagnostic platform. The invention provides for a simple means to monitor proper fluid flow, and potentially to correct for disturbances, enabling quantitative measurement, even should a tolerable failure occur. FIG. 7 provides an example of this. FIG. 7A is an image of a pulse obtained from a channel in which a bubble had formed between the fluid inlets and the imaging area. While no evidence of the bubble is otherwise present in the imaging area (and therefore may go undetected in a real-use device), the shape of the pulse itself indicates the presence of a flow disruption and therefore enables error detection. FIG. 7B shows a difference image of the functionalized surface following exposure to a number of antibody-containing pulses represented by the one shown in FIG. 7A. A priori of knowledge of the specific failure mode, the image provides data regarding the concentration and distribution of solutes in the pulse. Qualitative inspection of the distribution of adsorbate in FIG. 7B reveals an inhomogeneous distribution (greater coverage on the left side relative to the right.) The combination of the image data obtained from solute distribution and the adsorbate coverage will enable either error detection or correction, once the exact details of a correlation algorithm have been developed.

As another example, a device with slightly greater complexity was designed. This device had the loading Tee (orthogonal injection channel) on a separate layer, and the sample was injected into the main channel from this upper layer through a small hole in the intermediate layer. The dispersion function produced was striking, and quite unexpected in its shape. It may be difficult to predict, absent computationally-intensive numerical simulations of a given device geometry, what the concentration and distribution of solutes flowing over the sensor would be in this case. However, the present invention simply images the solute dispersion, providing a direct measurement.

Figure 8A:
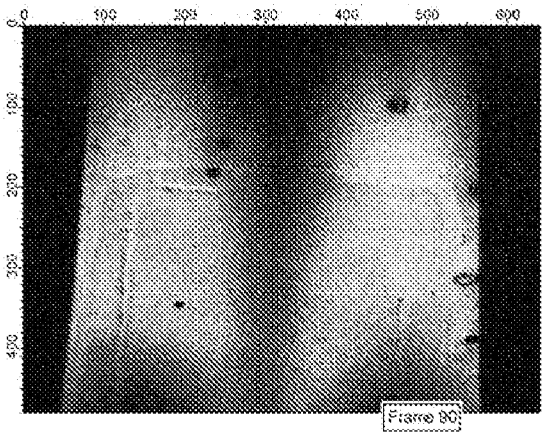
FIGS. 8A-8B. Image of complex, varying dispersion function and flow disturbances. Predicting such complex dispersion functions from a given device design is difficult and requires significant computational resources empirical monitoring of the actual fluid behavior of each device greatly simplifies the interpretation of the distribution of molecules on the functionalized sensor surface.
Figure 8B:
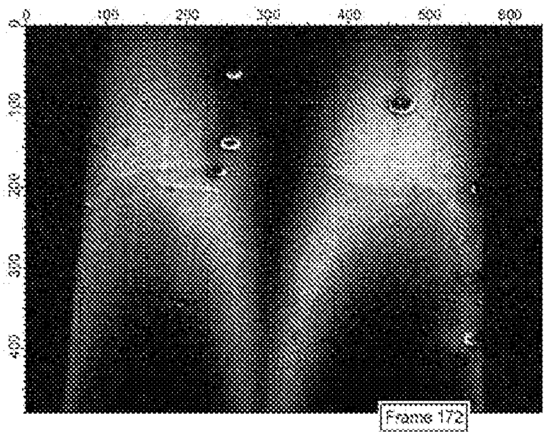
Figure 9:
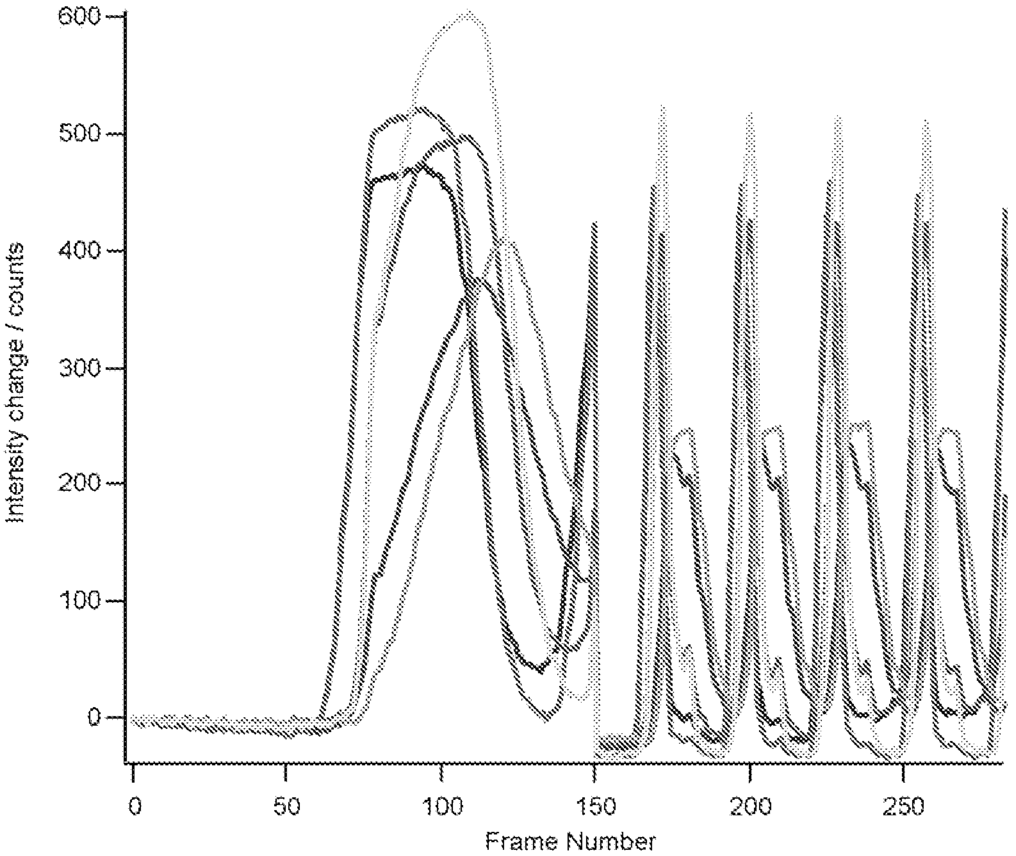
FIG. 9. Intensity vs. time plot obtained from experiment with errors in early injection sequences.

Several other features are evident from FIG. 8 and the related intensity data shown in FIG. 9. Firstly, the initial sample injection, as a result of an error in the pump operation, was significantly longer in duration and somewhat higher in concentration than the subsequent pulses. Secondly, small manufacturing variations in this device (which cannot be predicted, and therefore numerically simulated) resulted in the solute concentration on the right side of the channel to be slightly higher than on the left, as witnessed by the color being more yellow than orange, thirdly the presence of small bubbles in the channel (near the upper areas of the image) can be seen to slightly disturb the flow (see upper-left corner of FIG. 9B.) Again, the image data obtained as the pulses flow over the sensor can be used to monitor, detect, and correct for the high complexity, relatively low precision, and possible disturbances of the solute dispersion in these devices.

Example 7

Simple Microfluidic Device for Delivering a Calibrated Set of Reagent Dilutions to an Imaging Sensor This example describes an easily constructed polymeric laminate device that conducts a basic set of operations including, but not limited to, readily accepting a sample fluid, preparing a series of reagent dilutions, mixing them into a sample and delivering the mixtures to a sensor for analysis. The device conducts these operations in a novel and powerful format. The example describes its operational features using data obtained from a miniature Surface Plasmon Resonance imaging instrument.

The card design and operational principle described here can accomplish all the necessary functions when used with a reusable reader that controls fluid flow. The card is a simple laminate design, with four of the five layers laser-cut from Mylar or PMMA and mounted using pressure-sensitive adhesive onto a gold-coated glass slide with a pre established surface pattern. The experimental details shown here were obtained using a miniature surface plasmon resonance imager, though the operational concept of the card is, in principle, compatible with other image-based detection strategies such as colorimetry or fluorescence.

Principle of Operation

Figure 10A:
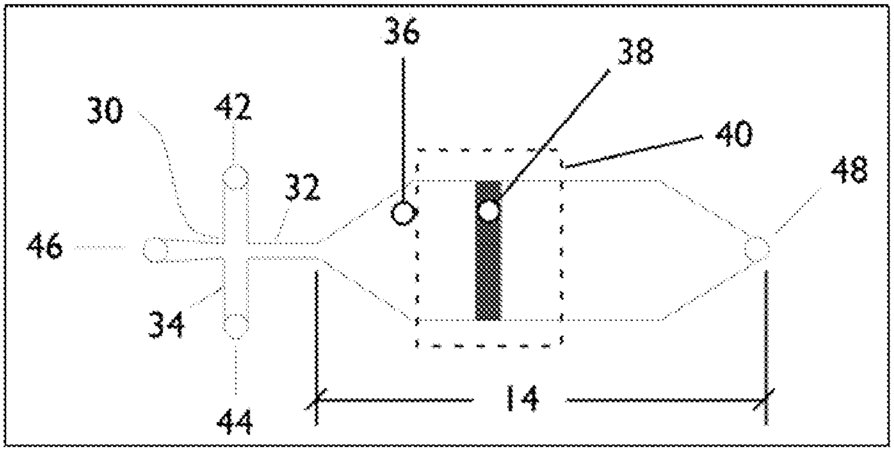
FIGS. 10A-10D. Microfluidic device geometry (10A), method of operation (10B), SPR difference image data (10C) and time series line profiles (10D).
Figure 10B:
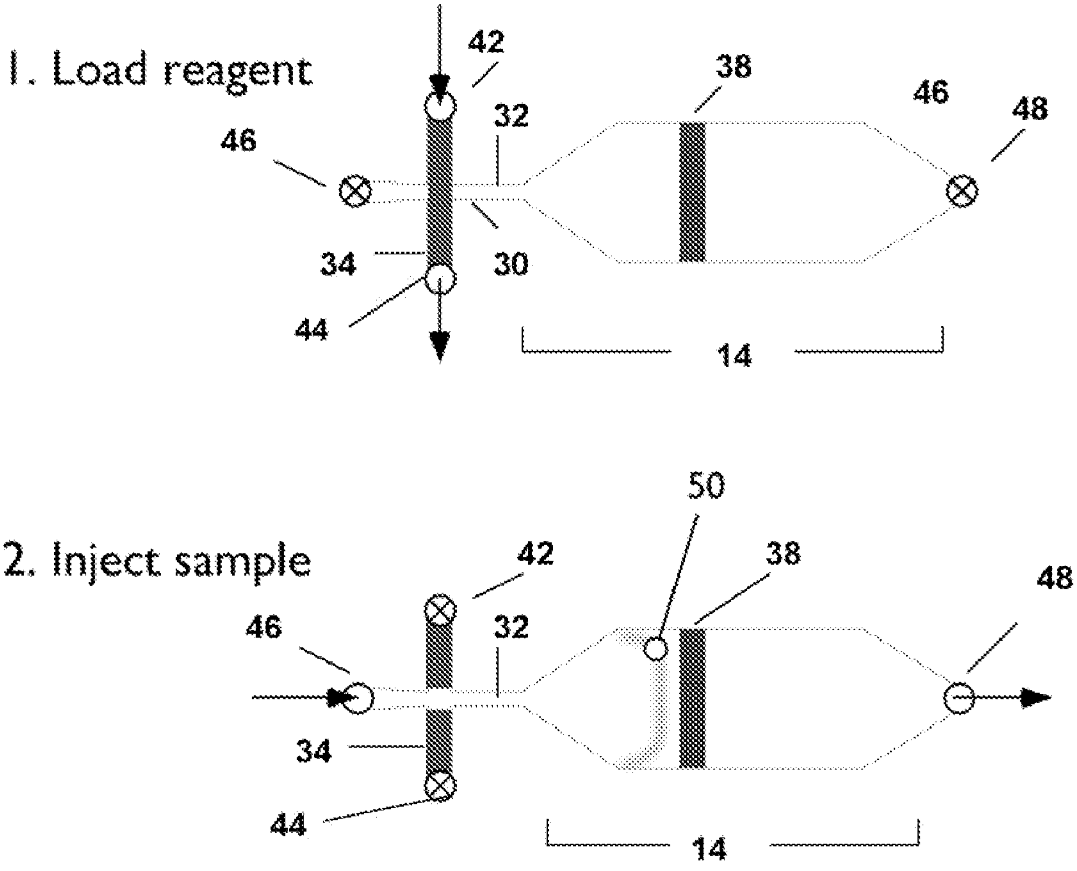
Figure 10C:
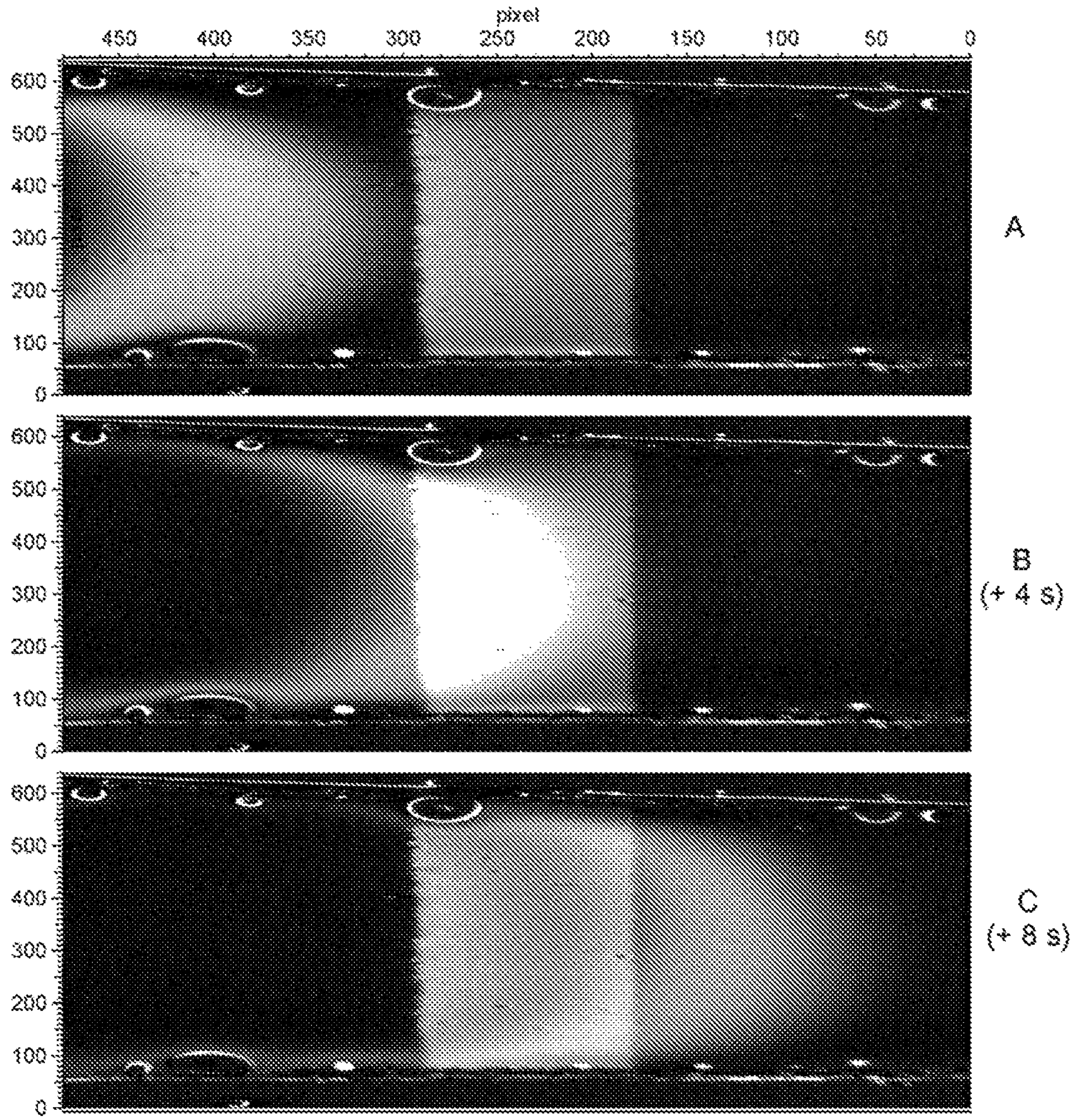

The device design is simple and familiar to many. It uses an injection tee 30 (FIG. 10A-B) to displace a portion of a sample fluid from a channel 32 using a small plug of reagent. Flow down this channel 34 alternates with sample flow along the main (input) channel 32, resulting in a series of pulses of reagent traveling down the main channel 14 interspersed by the sample fluid. In contrast to microfluidic designs for on-card electrophoresis or electrokinetic flow, here the plug is loaded and injected with pressure-driven flow. This leads to Taylor dispersion of the reagent into the sample producing inverse gradients of reagent and sample concentration around the reagent pulse, as in FIA systems.

An important step is the addition of a tracer compound to the reagent to enable the tracking of a co-migrating unlabeled compounds (antibodies, for instance). Using a tracer with an imaging detector enables run-time monitoring of the actual reagent concentration and distribution achieved in the experiments and correlation of this information to the data provided by the active biosensor surface.

Device Manufacturing

Soda-lime glass microscope slides were UV-ozone cleaned for 30 minutes under O2, then coated with 4.5 nm gold by e-beam evaporation (base pressure<1E-6 torr).

Surface patterning was accomplished using a commercially available airbrush mounted on a custom-built motion controller. The gold slides were mounted on a tray under a mylar contact mask containing openings to permit a spray of a 2 mM solution of functionalized thiols to come into contact with the gold coating of the substrate. Once the solvent had evaporated, the mask was removed and the slide flooded with 1 mM PEG thiol in ethanol to passivate the remaining surface. A laminated microfluidic device was placed on top of this substrate. It consisted of four laser-cut layers of mylar, 62 micron layer for assay and reagent channel covered by a mylar via/cap, 300 micron dilution layer, 2.5 mm acrylic cap with ports for off-card pumps. Cross-sectional dimensions of the assay channel are 0.060±0.005 mm×6.00±0.2 mm.

Figure 11:
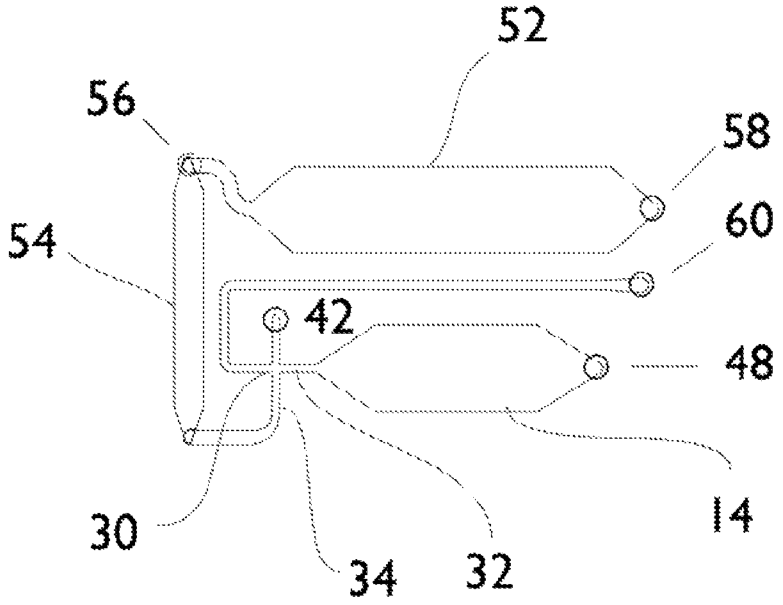
FIG. 11. Dispersive dilution device design and operation. The device layout is shown, with ports indicated by number (42, 48, 46, 58, 601-5). The assay channel 14 with the injection tee 30 is on the bottom, and is connected to the reagent channel 52 by an additional "dilution" channel 54. Buffer and reagent are loaded into the device through ports 48 and 58, respectively. Excess buffer exits the device through ports 56, 60, and 42, and excess reagent exits through port 56. Port 56 is then closed such that pushing reagent into port 58 will cause it to flow into the dilution channel 54 and out port 42, delivering a plug of reagent into the injection tee 30 at the intersection of the input channel 32 and the injection channel 34. A gradient of increasing reagent concentrations is created at the injection tee 30 by flowing only a fraction (~10%) of the total volume of the dilution channel 54 during each loading cycle. Dispersive mixing between the reagent and buffer in the dilution channel 54 leads to a sequentially increasing concentration of reagent in the pulse. Eventually, the buffer in the dilution channel 54 is fully washed through and the reagent concentration at the injection tee 30 reaches the concentration of reagent loaded into the device.
Figure 14A:
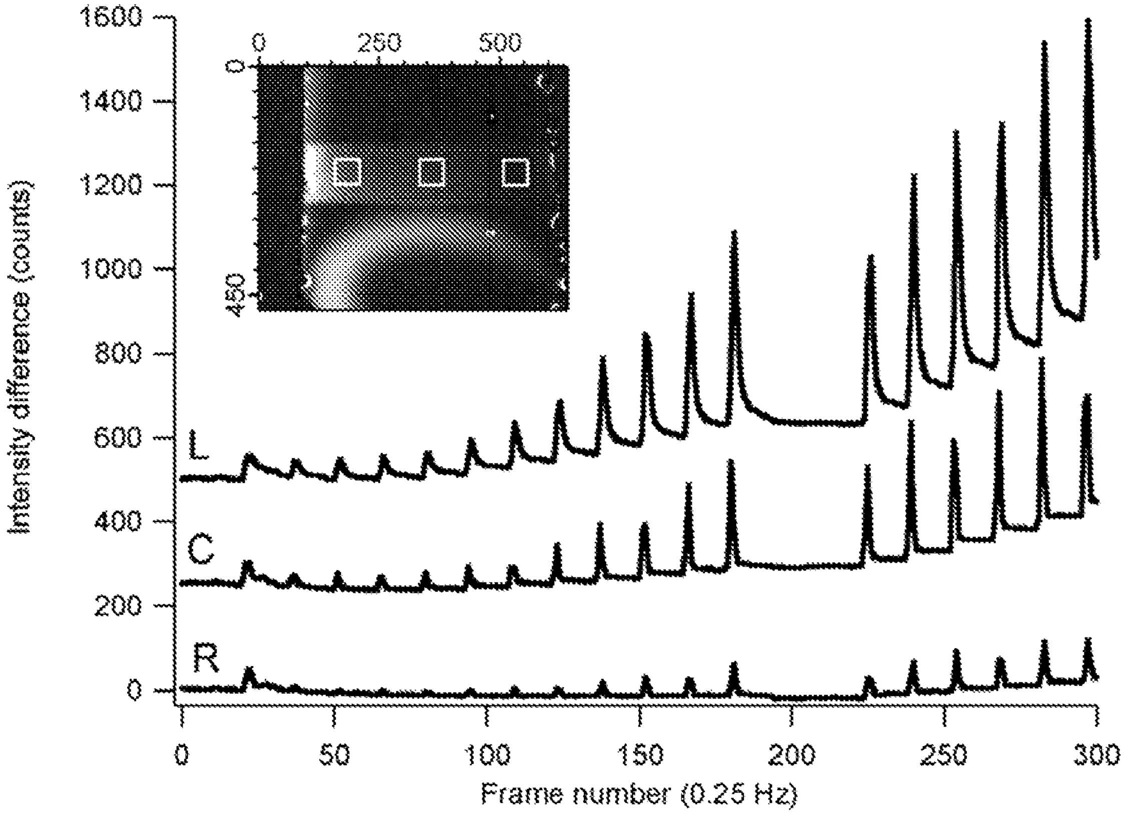
FIGS. 14A-14B. Integrated tracer signal correlates to change in surface coverage. (14A) Tracer intensity measured at three channel positions (white squares, inset) plotted versus time. Flow irregularity caused by a bubble upstream of the imaged area resulted in a highly non-uniform pulse shape (inset). This non-uniform solute distribution is captured in the varying relative pulse intensities at three channel locations and results in non-uniform distribution of bound solute. A linear result is obtained from the same data by integrating the tracer intensity with respect to time over narrow sections of the channel and plotting the result against the change in surface coverage following each pulse (14B). Traces L and C in FIG. 14A are offset in Y for clarity of presentation.
Figure 14B:
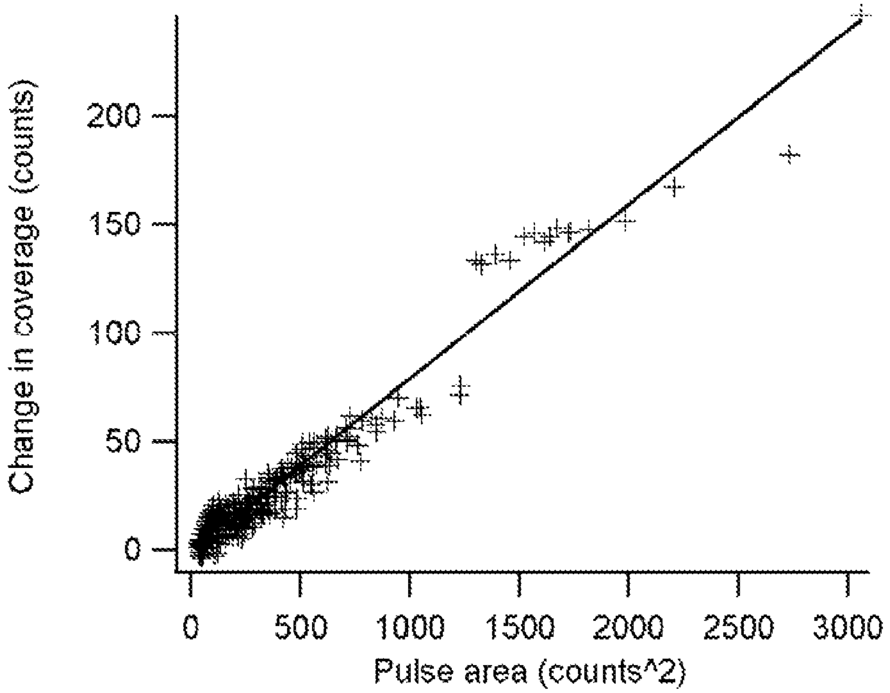

Tubing from pumps and sample loops are fed through and fastened to a thick acrylic block. An o-rings is fitted over the ends of the tubing protruding underneath the block. This fitting is then clamped to the device such that the tips are inserted completely into the holes in the acrylic layer of the device and the o-ring surrounding the tubes providing the seal. Fluids were loaded into the device using a similar fitting. The two solutions (sample and reagent) were loaded as follows: two syringes filled with one of the two liquids were coupled to ports 2 and 4 (FIG. 14). Next, the sample was pushed into the device until it flooded everything except the reagent channel, (plugged at the outlet by the other syringe.) Large bubbles and excess sample fluid exited out all open ports. Once this portion of the device was filled, the reagent solution was pushed into the (stilt dry) reagent channel, exiting from port 1 (FIG. 11). Port 1 was then plugged such that fluid would flow between the reagent and assay channels through the dilution channel connecting them. Finally, ports 2, 3, and 5 were connected to stepper-motor controlled syringe pumps, and port 4 left open to waste.

The syringe pumps were programmed to simultaneously push and pull 1.2 μL through ports 2 and 5, respectively. This flow is then stopped and 5 μL of sample fluid is pushed into port 3 (200 nL/sec, MLV=0.53 mm/sec), driving the plug of reagent into and along the assay channel.

The compact SPR-imaging instrumentation used in these experiments has been described in detail elsewhere. Briefly, an 8-bit 640×480 CCD camera measures the reflectivity from a collimated, TM polarized 850 nm LED output passed through set of folded optics and refractive index matched to the bottom of the microfluidic device such that the active portion of the fluidic channel is being imaged by the camera, SPR conditions are tuned by translating the LED across the optical axis until the reference areas of the image have a reflectivity value at the bottom of a pseudo-linear portion of the SPR curve (reflectivity ~1.3× minimum). 45 images (40 ms integration, 0.5 Hz frame rate) are co-added into a 16-bit result. Instrument calibration with a series of various RI standards is 1 count per 1E-6 RIU with a practical resolution of 3E-5 RIU (1 S.D.) and a linear dynamic range >3000 counts. Due to optical foreshortening, each pixel images 17.5×10.9 microns (X, Y respectively).

Refractophore samples were prepared in running buffer (Dulbecco's phosphate buffered saline, pH 7.3, thermally equilibrated with the pump system) by adding sufficient quantities (typically 2-10 mg/mL) of various compounds ("refractophores") including dextrose (MW 180.11), PEG-amine (Laysan bio, MW 20 000), dextran (leuconostoc, MW 71 000 Da), and purified mouse IgG (MW~150 000) so that the RI difference between the refractophore solution and the running buffer was 1E-3 RIU.

Device Operation—Pulse Formation and Analysis

Figure 10D:
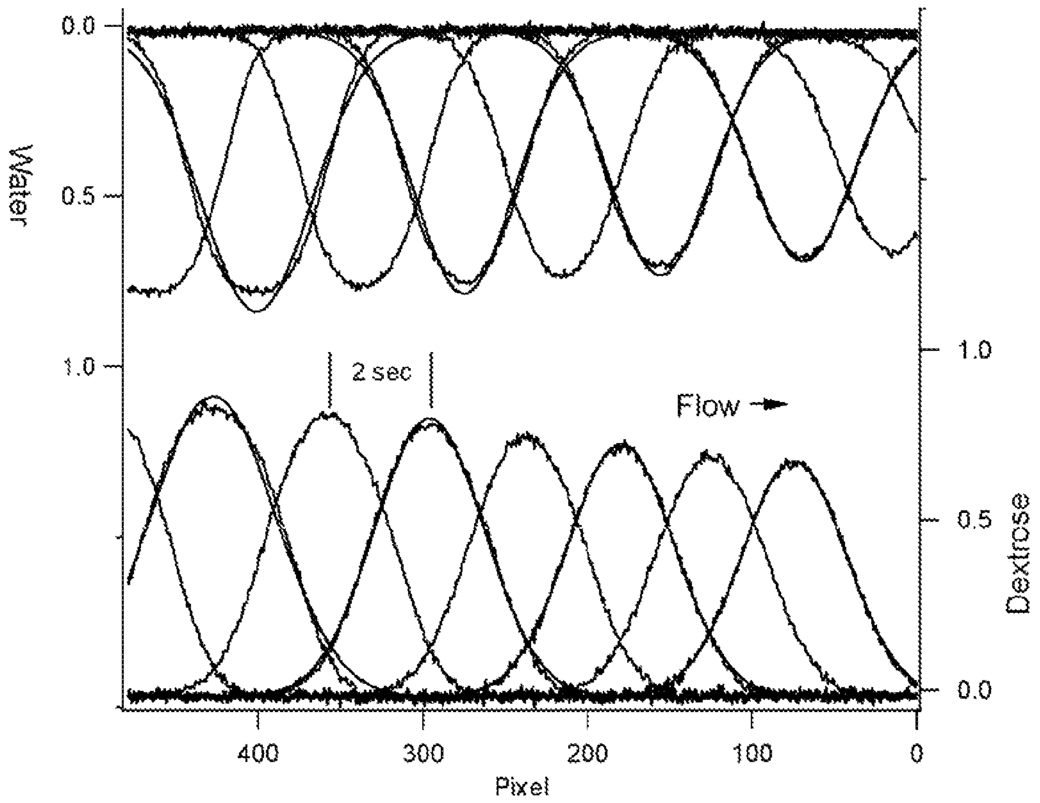

Reagent concentration and distribution in pulse is measured using a co-migrating tracer. In this case, the tracer is a refractophore (tracer), which is an inert solute added to the reagent at a concentration high enough to change the bulk refractive index of the reagent solution. Since the change in intensity of the SPR signal is linear with refractive index over a wide range, the intensity of the pulse reports on the concentration of refractophore, and thus indirectly reports the concentration of reagent in the pulse. Since the pulse is diluted by dispersion into the sample, the pulse intensity is inversely related to the concentration of sample in this region. This is shown in FIG. 10D, comparing the pulse shape and amplitude of a water pulse injected into buffer and a buffer plus dextrose pulse injected into buffer.

Measuring flow velocity, solute distribution, channel conditions, correlating to degree of surface binding. To improve statistics (and work towards the method of standard addition), a range of concentrations can be prepared in a single device.

Dispersive Dilution Card Loading and Output

Including an additional channel between where the reagent is loaded onto the card and the injection tee enables the card to prepare a series of reagent dilutions over a number of pulse injections (FIG. 11). The reagent is loaded into a dry channel (to prevent dispersive dilution of the reagent during loading), and the remainder of the device is loaded with buffer. Excess fluid (both reagent and buffer) exit a common port, resulting in a sharp boundary between the buffer at the entrance to the dilution channel. Once the device is filled, this port is plugged for the reminder of the experiment. Reagent is loaded into the injection tee by pushing fluid into port 2 white simultaneously pulling the same volume from port 5 (FIG. 11). Loading the injection tee with volume less than the total volume of the dilution channel (e.g., flowing a total of 1 μL for each pulse through a dilution channel whose total volume is 15 μL) results in a low initial reagent concentration at the injection tee. Each additional pulse has a higher reagent concentration until the dilution channel has been fully swept of buffer and the pulses are loaded with the stock reagent concentration.

Figure 12A:
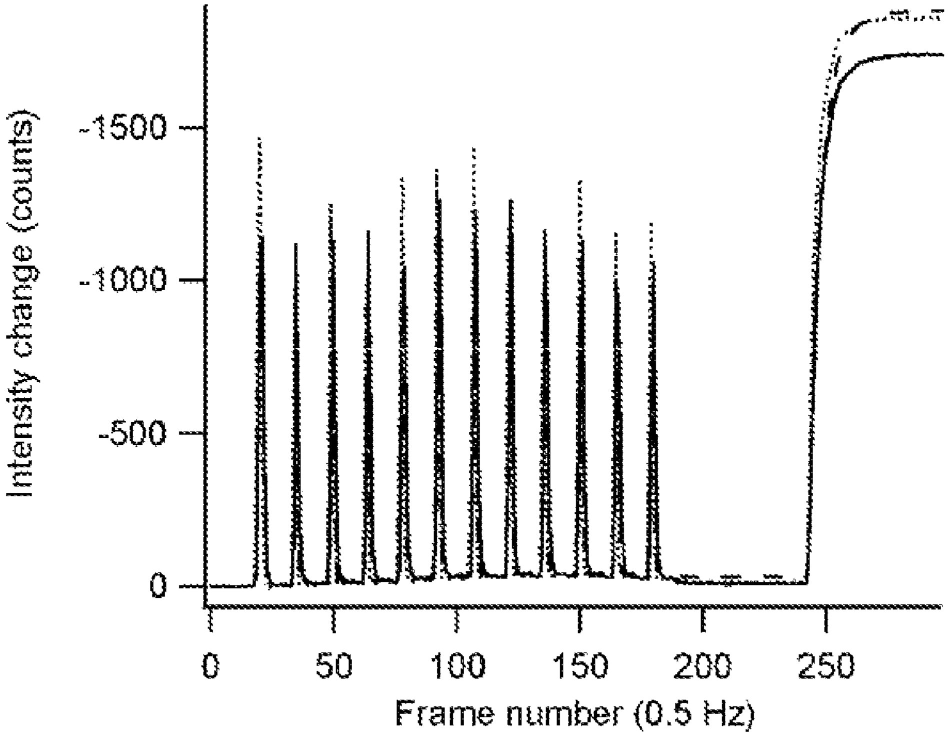
FIGS. 12A-12B. Pulse amplitude sequence for water (12A) and dextrose (12B) using dispersive dilution and pulse injection. (12A) pulse series created by filling the reagent and dilution channels with water and the assay channel with buffer, showing consistent pulse amplitudes, indicating that the sample dilution in the main channel is essentially independent of pulse number. The y axis as been inverted to facilitate comparison with (12B) (since water has a lower refractive index than buffer). Dispersive dilution of a dextrose solution loaded into the reagent channel is illustrated in (12B) using the same pump sequence as in (12A), except that the dilution channel was initially filled with buffer. Both (12A) and (12B) include floods, where reagent is flowed continuously into the assay channel until it reaches a steady-state value, which is used to determine the relative dilution factor of the reagent in each pulse compared to the initial concentration of reagent loaded into the device. Pulse area varies by ~10% across the channel for each pulse and ~13% among pulses. Flood data provides for actual concentrations of sample and reagent in each pulse (normalized intensity). Dextrose increases in concentration, but water does not; shows that dilution of sample is same regardless of dextrose concentration in pulse. Refractophore (dextrose here) reports on reagent concentration and sample dilution and their associated distributions.
Figure 12B:
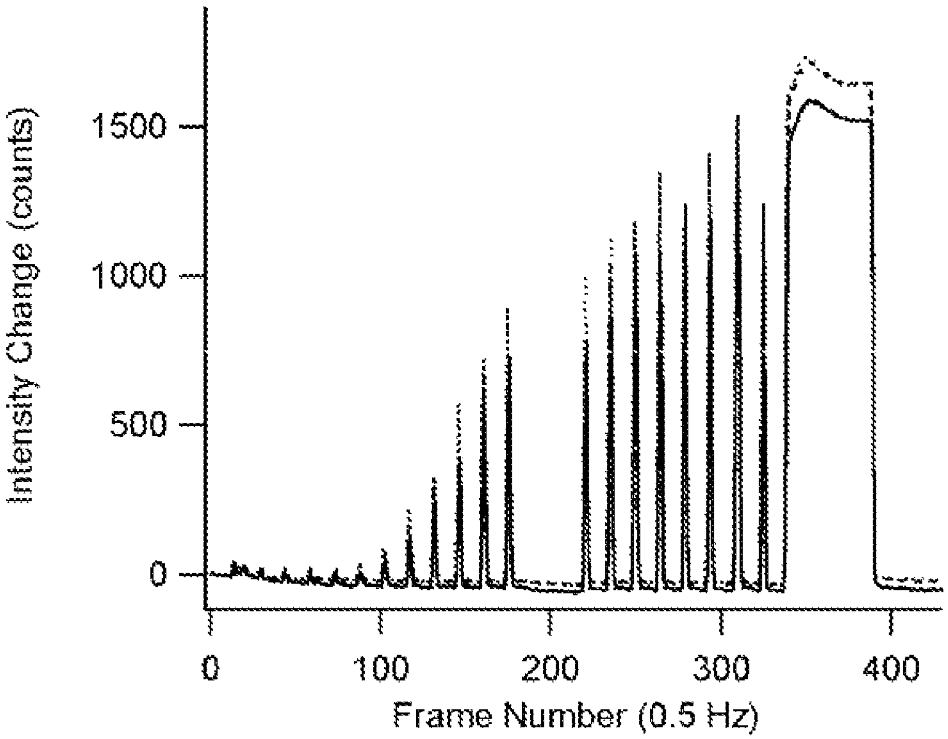

This result is illustrated in FIG. 12. Sample displacement as a result of pulse loading is measured by filling the dilution channel with water and injecting water pulses into the buffer-filled assay channel (FIG. 12A). As each pulse is formed using the same programmed syringe displacement, the pulse height and areas are identical to within 10%. Filling the reagent channel with a buffer solution containing 2.0 mg/mL dextrose and loading this reagent through a dilution channel filled with buffer (no dextrose) leads to the increasing reagent concentrations in the pulse series shown in FIG. 12B. Taken together, FIGS. 12A and 12B show how the sample dilution is essentially identical for each pulse, whereas the reagent concentration steadily increases up to its maximum value. The actual concentration of solute in each pulse can be determined by comparison with the flood intensity, determined by continuously flowing the reagent into the assay channel until the solution in the assay channel has been fully displaced with reagent.

Image Analysis

Figure 13:
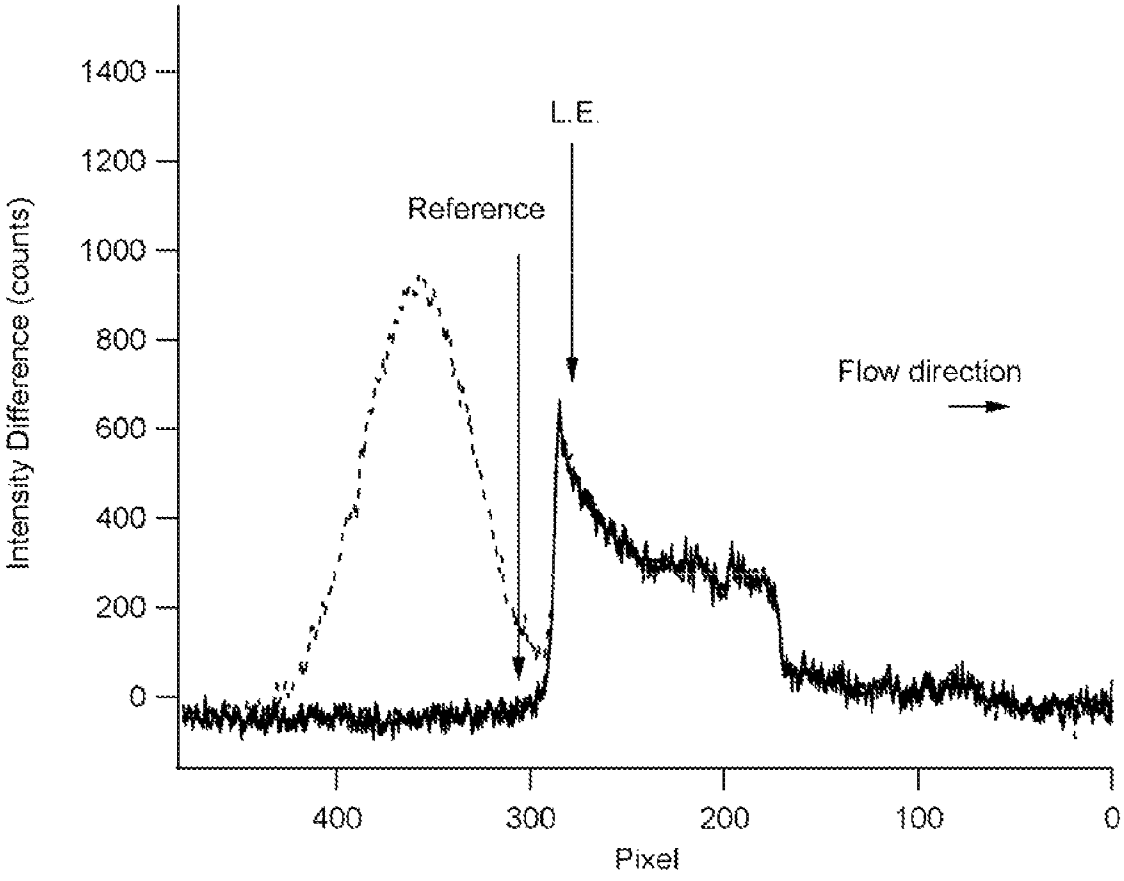
FIG. 13. Correlating surface adsorption to solution reagent concentration. Each pulse traverses a reference region before reaching the capture surface (between pixel 280 and 180 in this example). A snapshot of one pulse just upstream of the capture surface is shown here (dashed line). The concentration and distribution of reagent in the pulse is measured by monitoring the sensor response in the reference region generated by the inert, co-migrating tracer compound added to the reagent solution. Surface binding depletes solute from the pulse, resulting in decreased coverage further downstream in the binding surface and curved binding profiles (solid line). To correlate the amount of adsorption to the concentration of reagent, the integrated pulse area measured at the reference point is plotted against the change in intensity measured at the leading edge. (061808f)

The bimolecular interaction model stipulates that, assuming a single rate constant, the initial change in surface coverage with time will be linearly related to the concentration of solute adjacent to the surface (neglecting off-rate, prior surface coverage). Since the tracer intensity correlates to solute concentration (to a first approximation, see below), the pulse area is directly proportional to the solute concentration and interaction time. The pulse area can be calculated by integrating the intensity over pulse width at a reference position immediately upstream of the binding surface (FIG. 13). The change in surface coverage is calculated at the leading edge of the binding surface, because coverage drops off rapidly downstream of this point due to depletion of solute in the pulse. This calculation is conducted at a number of positions across the channel. A linear correlation between change in surface coverage vs. pulse area is obtained from the card operation, even if pulse shape is non-uniform (FIG. 14).

Monitoring Dispersion

Figure 15:
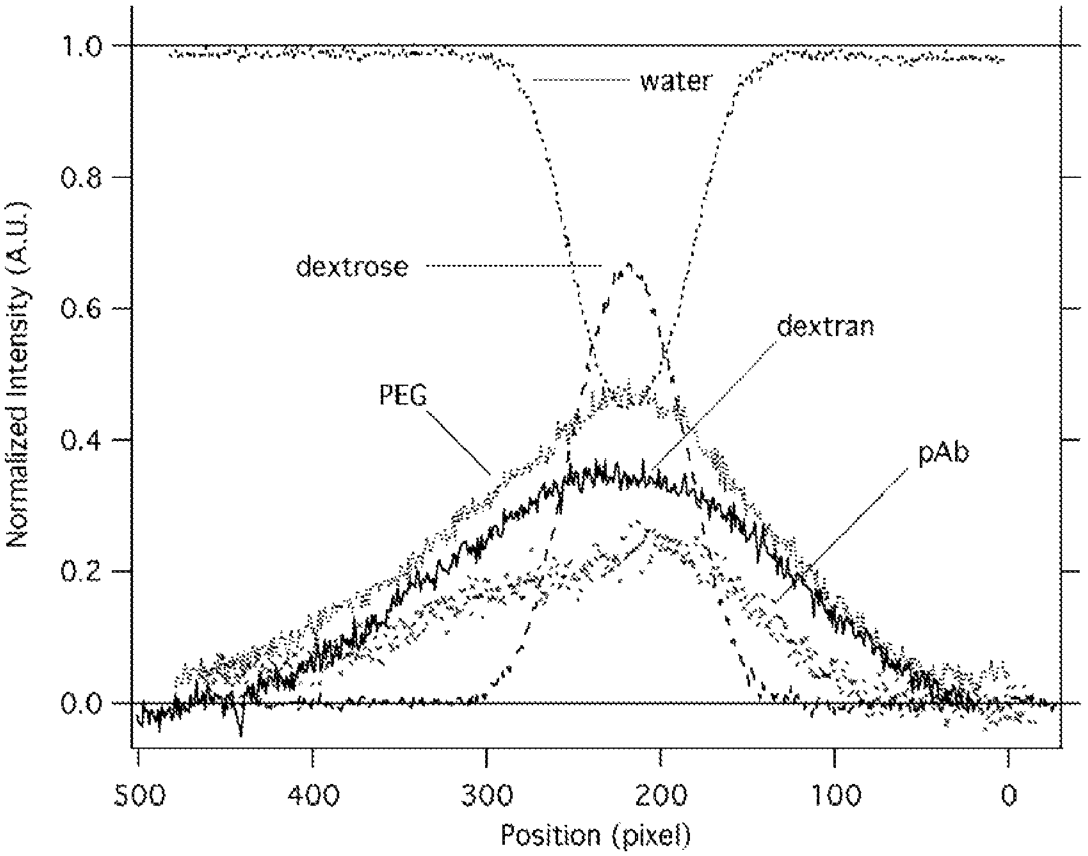
FIG. 15. Comparison of varying molecular weight tracer distributions. Solutions of PBS plus dextrose (180 Da), PEG (20,000 Da), dextran (71,000 Da), and purified rabbit IgG (150,000 Da) were injected into a PBS carrier to measure and compare the dispersion of solutes over this molecular weight range. The pulse intensities were flood-normalized to a flood intensity of refractophore concentrations adjusted to produce similar bulk refractive index changes. Relative dispersion behavior of slow diffusing species compared to small molecules distributes these molecules into the sample. Amplitudes were normalized to the flood intensity of each compound and corrected for each solution's bulk refractive index. The asymmetry of IgG is the result of chromatographic retention by the surface (5 mg/mL IgG solution strongly interacted with PEG surface). Data used to show degree of interaction between various dispersing species and sample containing small molecule analyte. Degree of mixing between pulse and sample can be evaluated by comparing the results from the appropriate refractophores.

Dispersive distribution of solutes with varying diffusivities can be measured using different refractophores species. FIG. 15 illustrates how the distribution changes with molecular weight of refractophore. Water pulses into a buffer-filled channel closely mirror a buffer plus dextrose pulse, showing how rapidly diffusing species (ions and small molecules) quickly equilibrate through the channel depth leading to sharp Gaussian profiles. More slowly diffusing species such as 20 kDa PEG, 70 kDa dextran, or IgG are more broadly distributed through the sample fluid. This shows how the interaction zones between the sample and reagent, along with their relative concentrations, can be measured and compared using a carefully chosen appropriate refractophore.

Competitive Immunoassay Results

Figure 16:
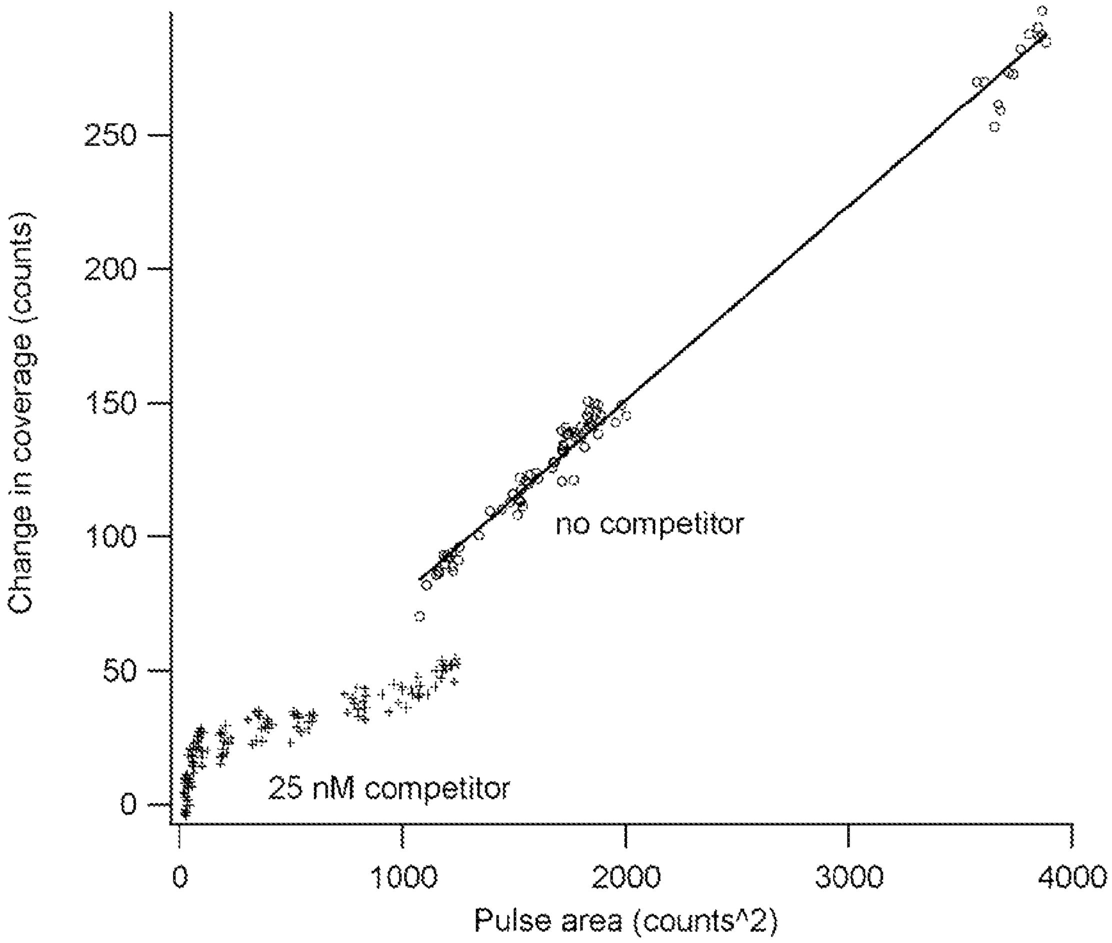
FIG. 16. Example of competitive immunoassay result, comparing change in coverage versus pulse area both with and without competitor present in sample fluid. Data were collected from a single device, first using 25 nM phenytoin in PBS as the sample fluid, running 12 pulses of 400 nM antiphenytoin antibody (plus 2 mg/mL dextrose), then washing the assay channel with buffer before running another 8 antibody pulses through PBS without competitor. The dilution channel was initially primed using 4 μL of reagent (constant flow) before starting the pulse sequence. The differential dispersion of the refractophore compared to antibody during this priming phase led to the initial rapid rise in coverage for small pulse areas (<100 counts$^2$).

The interaction between reagent and sample can be exploited to conduct a competitive immunoassay. If the sample fluid contains a small molecule analyte, the reagent consists of an antibody against the analyte, and the binding surface has been functionalized with the analyte (or an analog thereof). FIG. 16 illustrates this principle. In the absence of competitor in the sample fluid, antibody pulses of varying amplitude result in a linear response of pulse area versus change in coverage, as shown before. When the sample fluid contains a small molecule competitor (phenytoin, in this case), the amount of antibody adsorbed to the surface is decreased, and varies with pulse amplitude (i.e., antibody concentration).

CONCLUSIONS

This example describes a simple device that is easy to manufacture, load, and operate. The card interfaces with reusable instrumentation that provides fluid flow control. Dispersion resulting from pressure-driven flow is used to mix reagent into the sample and generate a series of varying reagent concentrations added to the sample fluid. Adding a tracer compound into the reagent enables monitoring of reagent concentration, distribution, and relative dilution. Tracer enables error tolerant operation. A linear response is obtained, even from irregular data. Dispersion is dependent on diffusivity of species. Card calibration is possible by comparing rates in presence and absence of sample.

Throughout this application various publications are referenced. The disclosures of these publications in their entireties are hereby incorporated by reference into this application in order to describe more fully the state of the art to which this invention pertains.

From the foregoing it will be appreciated that, although specific embodiments of the invention have been described herein for purposes of illustration various modifications may be made without deviating from the spirit and scope of the invention. Accordingly the invention is not limited except as by the appended claims.

What is claimed is:

1. A microfluidic assay system comprising:

(a) an input channel having an upstream end and a downstream end;

(b) an injection channel that intersects with the input channel between the upstream end and the downstream end of the input channel, wherein the injection channel has a receiving end and a terminus disposed at opposing sides of the intersection with the input channel;

(c) a reagent channel and a dilution channel, each having an upstream end and a downstream end, in communication with the injection channel, wherein the dilution channel is in series with and between the reagent channel and the injection channel;

(d) an assay channel having an upstream end, a downstream end, and a surface that receives fluid flowing from the downstream end of the input channel toward the downstream end of the assay channel;

(e) a capture region disposed on the surface of the assay channel and to which a detector molecule is bound; and (f) a reference region disposed on the surface of the assay channel;

(g) detection means for detecting an amount of binding between the capture region and an analyte and/or reagent and for detecting an amount of a tracer present in the reference region; and (h) analysis means in communication with the detection means and that correlates the amount of binding detected at the capture region to the amount of tracer detected in the reference region.

2. The system of claim 1, wherein the injection channel is orthogonal to the input channel.

3. The system of claim 1, wherein the assay channel is at least twice as wide as the input channel.

4. The system of claim 1, further comprising four ports, each port permitting fluid flow therethrough when open, wherein a port is located at each of the following: at the upstream end of the input channel, at the receiving end of the injection channel, at the terminus of the injection channel, and at the downstream end of the assay channel.

5. The system of claim 1, further comprising five ports, each port permitting fluid flow therethrough when open, wherein a port is located at each of the following: at the upstream end of the reagent channel, between the reagent channel and the dilution channel, at the upstream end of the input channel, at the terminus of the injection channel, and at the downstream end of the assay channel.

6. The system of claim 1, wherein the reference region is at least partially coextensive with the capture region.

7. The system of claim 6, wherein the detection means for detecting an amount of a tracer present in the reference region detects a tracer molecule that co-migrates with a molecule that binds to the capture region.

8. The system of claim 7, wherein the detection means for detecting an amount of a tracer present in the reference region detects a tracer conjugated to a molecule that binds the capture region.

9. The system of claim 1, further comprising a pressure-driven flow means for delivering a solution into the injection channel.

10. A method of detecting an analyte in a microfluidic sample, the method comprising:

(a) delivering via pressure-driven flow a solution containing a reagent that binds the analyte and a tracer into the receiving end of the injection channel of the system of claim 1;

(b) delivering a sample fluid suspected of containing the analyte into the upstream end of the input channel under conditions permitting flow of the sample fluid toward the downstream end of the assay channel and permitting dispersion of the reagent into the sample fluid, wherein the analyte, if present, binds to the reagent;

(c) detecting the amount of tracer present in the fluid as it passes over the reference region and the capture region;

(d) detecting the amount of binding between the analyte and/or reagent and the capture region; and (e) correlating the amount of binding detected at the capture region to the amount of tracer detected in the reference region, wherein the amount of binding relative to the amount of tracer is indicative of the relative amount of analyte present in the sample.

11. The method of claim 10, wherein the reagent is an antibody.

12. The method of claim 10, wherein the capture region comprises immobilized antibodies that recognize and bind the analyte or immobilized analyte analog.

13. The method of claim 10, wherein the method is performed without use of electrokinetic flow.

14. The method of claim 10, wherein the delivering via pressure-driven flow comprises use of a pump, gravitational pressure, bubbling, capillary forces, or negative pressure.

15. The method of claim 14, wherein the pump comprises a programmable syringe pump.

16. The method of claim 10, wherein the detecting comprises surface plasmon resonance (SPR).

17. The method of claim 10, wherein the detecting comprises total internal reflection.

18. The method of claim 10, wherein the detecting comprises colorimetry or fluorescence detection.

19. The method of claim 10, wherein the delivering of step (a) is modulated by use of ports disposed at each of the receiving end and the terminus of the injection channel.

20. The method of claim 19, wherein the delivering is modulated by closing the ports upon filling of the injection channel with the solution.

* * * * *